United States Patent [19]

Jennings et al.

[11] Patent Number: 5,225,331
[45] Date of Patent: Jul. 6, 1993

[54] IMMUNOASSAY FOR DETECTING GROUP B STREPTOCOCCUS

[75] Inventors: Harold J. Jennings, Gloucester, Canada; Francis Michon, Ottawa, Canada; Robert J. Chalifour, Laval, Canada; Martial Lacroix, Laval, Canada; Robert Feldman, London, England; Dennis L. Kasper, Boston, Mass.; Vince Pozsgay, Rockville, Md.

[73] Assignees: National Research Council of Canada, Ottawa, Canada; President and Fellows of Harvard College, Cambridge; The Brigham and Women's Hospital Inc., Boston, both of Mass.

[21] Appl. No.: 691,310

[22] Filed: Apr. 25, 1991

[51] Int. Cl.$^5$ .................. G01N 33/569; C07K 15/00; C07K 15/28
[52] U.S. Cl. .................. 435/7.34; 435/7.9; 435/7.94; 435/29; 435/259; 435/975; 435/961; 530/388.4; 530/389.5; 530/391.1; 530/391.3
[58] Field of Search .................. 435/7.34, 7.9, 7.92, 435/7.94, 961, 962, 975; 530/389.5, 391.1, 391.3

[56] References Cited
FOREIGN PATENT DOCUMENTS
250561 8/1988 European Pat. Off. .......... 435/7.34

OTHER PUBLICATIONS

Feldman et al, J. Clin. Pathol., 39:223–226 (1986).
Michon et al, Biochemistry, 27:5341–5351 (1988).
Wald et al, J. Clin. Microbiol., 25(3):573–574 (1987).

Primary Examiner—David Saunders
Assistant Examiner—Carol E. Bidwell
Attorney, Agent, or Firm—Nixon & Vanderhye

[57] ABSTRACT

Immunoadsorbent combinations for the detection and diagnosis of group B streptococcus polysaccharide antigen, comprising an insoluble carrier, a capture agent having an affinity for specifically binding to the trirhamnose epitope of group B streptococcus antigen and having the formula $\alpha$-L-Rhap(1→2)-$\alpha$-L-Rhap(1→2)$\alpha$-Rhap-1- wherein Rhap is rhamnose, and an antigen marker agent having an affinity for binding to monorhamnose epitope of group B streptococcus polysaccharide antigen of formula $\alpha$-L-Rhap-1- when the group B streptococcus polysaccharide is bound to the carrier. An immunoassay method test kit and polyclonal antibody are also described.

55 Claims, 12 Drawing Sheets

IMMUNOASSAY FOR DETECTING GROUP B STREPTOCOCCUS

The present invention relates to the detection of Group B streptococcus (i.e. streptococcus agalactiae) polysaccharide antigen in fluids, such as test solutions and body secretions. The present invention also relates to the detection or diagnosis of Group B streptococcus infection in mammals, including humans, and other types of animals, such as cows.

BACKGROUND OF THE INVENTION

Immunoassays are well known for detecting substances which may be involved in immunoreactions. Detection of such a substance, for example in a test solution, may be carried out by incubating the solution with a marker agent and then establishing whether any marker agent is bound to the substance present in the solution. The marker agent may comprise any material which can bind to the substance and which is also labelled with an assay tracer. An assay tracer may comprise a radioactive isotope or some other chemical/biological labelling component upon which the assay may be based.

Immunoassays are available in different formats, for example as an ELISA (i.e. an enzyme-linked immunosorbent assay), such as a single use device (SUD), as a latex agglutination format and as a radioimmunoassay. The ELISA relates the presence of a substance (for example an antigen or antibody) to enzymatic activity. In this type of assay, the substance is detected using a marker agent provided with an enzyme label (see for example U.S. Pat. Nos. 3,791,932; 4,757,134 and 4,833,071). An ELISA also uses an immunoadsorbent composition for capturing the substance of interest prior to the detection thereof.

The SUD typically comprises a membrane carrying a capture antibody to which the antigen under investigation binds. A "sandwich" is then formed using a second marker antibody carrying a suitable label such as an enzyme which is subsequently contacted with a substrate to form a color.

In the latex agglutination format, the antigenic material is adsorbed onto polystyrene beads in the form of latex having a milky appearance. Subsequent addition of the antibody causes agglomeration of the coated latex particles with a consequential change in visual appearance of the medium.

A radioimmunoassay is the same as an ELISA except that the enzyme is replaced by a radioisotope for example iodine 125. Detection is effected using a gamma counter.

Group B streptococcus (GBS) infection constitutes a serious health threat to humans and animals. GBS infection, for example, is the cause of mastitis in dairy herds. Of particular concern, however, is the occurrence of GBS infections at the time of childbirth. Expectant mothers who are carriers of this bacterium are exposed to a risk of postpartum infection, but they may also transfer the infection to their child as the child passes through the birth canal. Prevention of such infection in newborns is possible with preterm testing to identify cervical or vaginal carriage of GBS followed by antibody treatment when necessary (1). Rapid immunodiagnostic testing is preferable to overnight culture in this situation because of the need for the antibiotic treatment before parturition.

Group B streptococcus can be differentiated from other streptococcus by the presence of a group specific polysaccharide antigen ("C" substance) common to the five individual GBS serotypes (2, 3, 4). This common GBS polysaccharide antigen contains L-rhamnose, D-galactose, 2-acetamido-2-deoxy-D-glucose and D-glucitol (5, 6). The entire structure of the GBS polysaccharide antigen has previously been shown to comprise four different oligosaccharide units having the structures I, II, III and IV shown below (5, 6):

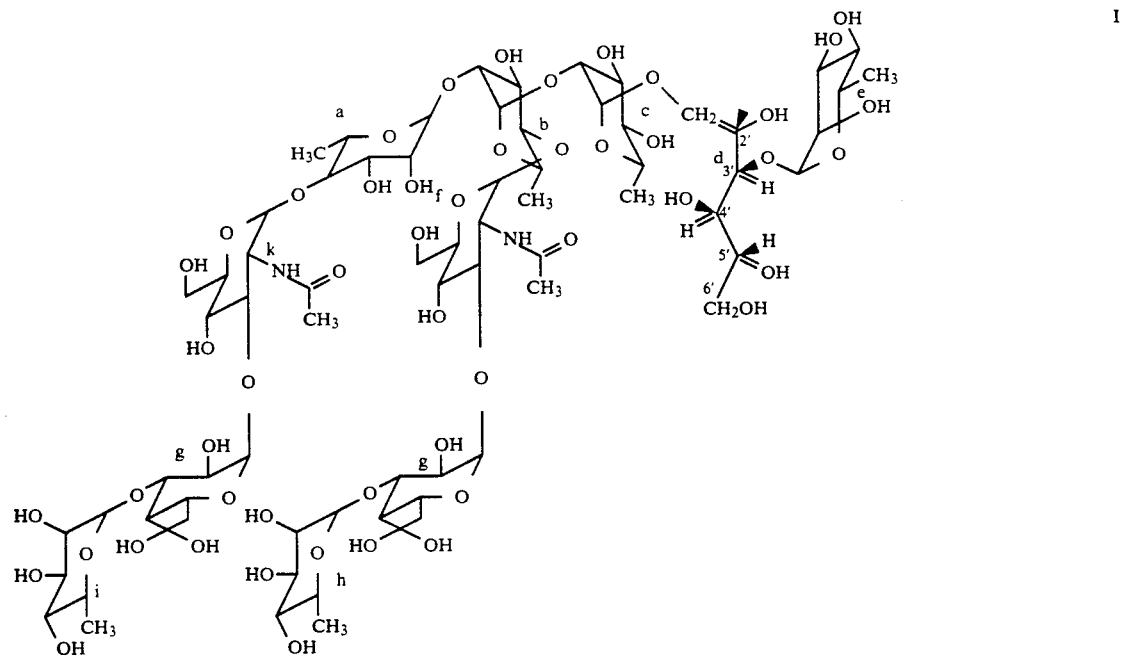

-continued
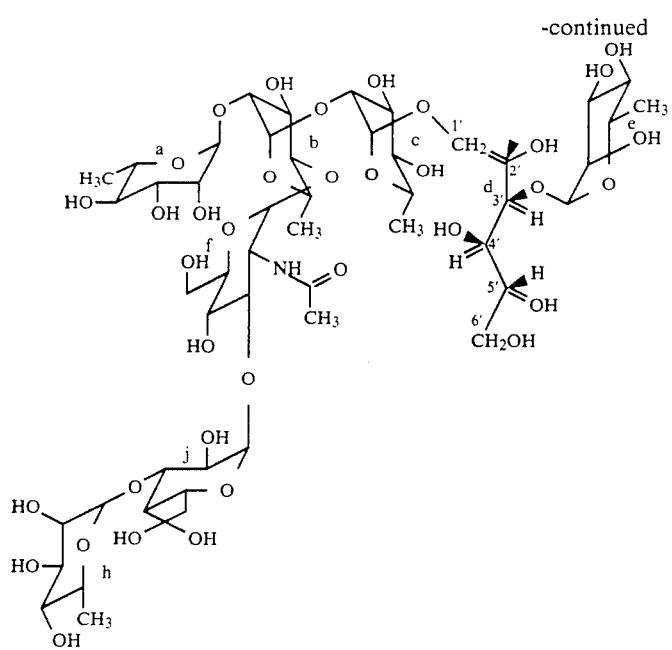
II
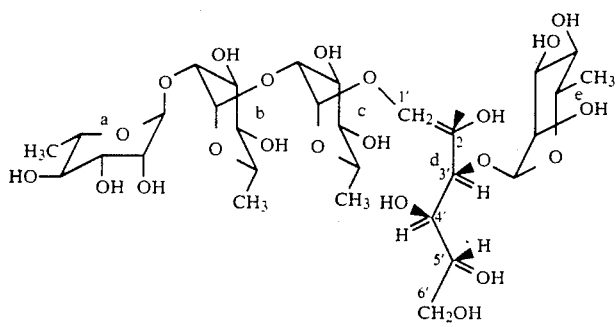
III
and
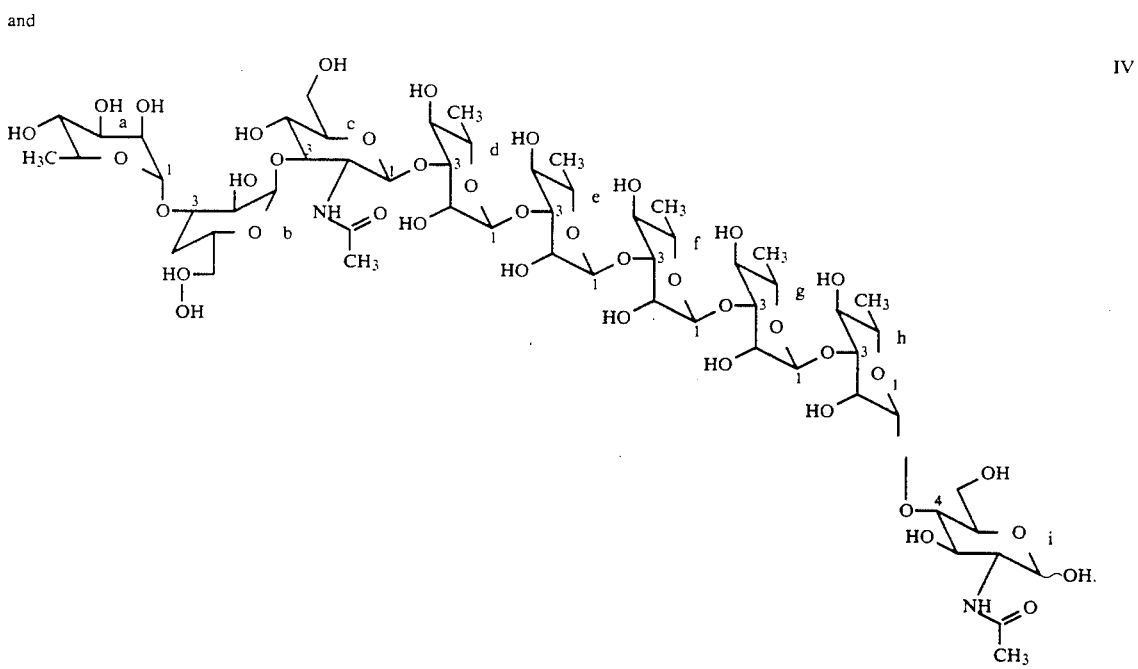
IV
The oligosaccharide units I, II, III and IV have been shown to be linked together by a type of phosphodiester linkage (i.e. between 06 of D-glucitol and 06 of D-galactopyranose) to form a complex highly branched multiantennary structure. The overall structure of the GBS polysaccharide antigen can be represented as follows (6).

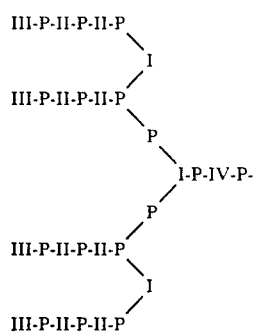

Immunodiagnostic assays for GBS target the GBS polysaccharide antigen (7). From structural studies, it is known that the GBS polysaccharide antigen has monorhamnose epitopes and 4 trirhamnose epitopes, and it is also known that the terminal monorhamnose group which includes the group of formula α-L-Rhap-1-, wherein Rhap is rhamnose, is an immunodominant epitope of the GBS polysaccharide antigen (8). However, this monorhamnose group is responsible for much of the cross-reactivity observed with the polysaccharides and antisera of streptococcus B, streptococcus G and streptococcus pneumoniae XXIII (9).

A number of studies have noted that certain commercial tests for GBS polysaccharide antigen, of the ELISA and latex agglutination types, lack sensitivity (10, 11), and may exhibit cross-reactivity with non-GBS bacterial antigens (12). In the case of expectant mothers, false results obtained as a result of such cross-reactivity can lead to unnecessary exposure of the unborn child to antibiotic therapy. Lack of sensitivity to GBS can lead to the more serious situation of failure to administer treatement, with the consequent increased risk of neonatal GBS disease.

The optimum time for screening expectant mothers has been reported to be at the onset of labor. There exists, therefore, a need for a relatively rapid diagnostic test of increased sensitivity and specificity (absence of cross-reativity) to diagnose the presence of GBS, especially in pregnant women immediately prior to childbirth. The present invention seeks to provide a rapid diagnostic test with superior sensitivity and specificity towards GBS.

SUMMARY OF THE INVENTION

The present inventors have undertaken a systematic study of epitopes to determine those epitopes having superior selectivity for GBS as compared to the monorhamnosyl epitope. The inventors have also investigated different assay formats to determine those which exhibit improved sensitivity to GBS.

The present inventors have discovered, surprisingly, that the monorhamnosyl epitope can be used effectively in the immunodiagnosis of GBS when used in conjunction with the trirhamnosyl epitope, for example in a two-site ELISA format. In this combination, the trirhamnosyl epitope, when used as capture epitope to bind to the capture antibody, contributes high specificity towards GBS, and the monorhamnosyl epitope, used as the target of the enzyme-labelled antibody, confers sensitivity and eliminates competition between the capture epitope and the enzyme-labelled antibody for binding to the capture antibody.

It has also been discovered that when the trirhamnosyl epitope is used as target for the capture antibody in a single-site ELISA format, the sensitivity to GBS polysaccharide antigen falls to near zero, in the significant range of <1 ng of GBS polysaccharide antigen, when the standard strategy of coating the maximum amount of capture antibody (in the region of 500 ng/well) is followed. It has been found by the present inventors that the single-site ELISA does function when the trirhamnosyl capture antibody coating density is reduced from about 500 ng/well to about 160 ng/well, although slight reduction in sensitivity towards the GBS polysaccharide antigen is observed.

In accordance with one aspect, the present invention provides an immunoadsorbent combination, comprising an antigen marker agent, an insoluble carrier, and an antigen capture agent immobilized to the surface of the insoluble carrier. The antigen capture agent has an affinity for specifically binding to trirhamnose epitope of GBS polysaccharide antigen to immobilize the GBS polysaccharide antigen on the carrier. The trirhamnose epitope comprises the group of formula α-L-Rhap(1→2)α-L-Rhap(1→2) α-Rhap-1-, in which Rhap is rhamnose. The antigen marker agent has an affinity for binding to GBS polysaccharide antigen when that antigen is bound to the carrier.

In accordance with another aspect, the present invention provides an immunoadsorbent combination for the detection of GBS polysaccharide antigen, comprising an antigen marker agent, an insoluble carrier, and an antigen capture agent immobilized to the surface of the insoluble carrier. The antigen capture agent has an affinity for specifically binding to monorhamnose epitope of the GBS polysaccharide antigen to immobilize the GBS polysaccharide on the carrier. The monorhamnose epitope comprises the group of the formula α-L-Rhap-1-, in which Rhap is rhamnose. The antigen marker agent has an affinity for specifically binding to GBS polysaccharide antigen when that antigen is bound to the carrier.

In accordance with a further aspect, the present invention provides an immunoassay method for the detection of group B streptococcus polysaccharide antigen. The method comprises the steps of:

(i) contacting a test solution suspected of containing GBS polysaccharide antigen with an antigen capture agent having an affinity for binding to the monorhamnose or trirhamnose epitope of GBS as defined above and immobilized on an insoluble carrier, and (ii) introducing an antigen marker agent having an affinity for binding to the GBS polysaccharide antigen when bound to the antigen capture agent to detect the presence of any GBS bound to the carrier.

In accordance with yet another aspect, the present invention provides a test kit for the detection of GBS polysaccharide antigen, comprising suitably in separate containers:

a) an antigen capture agent having an affinity for binding to monorhamnose or trirhamnose epitope of GBS as defined above immobilized to the surface of an insoluble carrier;

b) a first extraction agent for an aqueous nitrous acid extraction of GBS polysaccharide antigen from group B streptococcus bacteria, the first extraction agent comprising an organic acid;

c) a second extraction agent for an aqueous nitrous acid extraction of GBS polysaccharide antigen from group B streptococcus bacteria, the second extraction agent comprising an inorganic nitrite, the first extraction agent and second extraction agent being capable of reacting together to produce nitrous acid when admixed in an aqueous medium;

d) a neutralizing agent for neutralizing excess nitrous acid; and e) an antigen marker agent having an affinity for specifically binding to mono or trirhamnose epitope of GBS polysaccharide antigen when that antigen is bound to the carrier.

According to another aspect, the present invention provides an immunogen conjugate for stimulating antibody production against GBS polysaccharide antigen. The conjugate comprises a carbohydrate bound to a pharmaceutically acceptable carrier, the carbohydrate having immunoreactivity for stimulating antibody production against rhamnose epitope of GBS polysaccharide antigen. The rhamnose epitope is selected from (a) a trirhamnose group of formula α-L-Rhap(1→2) α-L-Rhap(1→2) α-L-Rhap-1-, (b) a monorhamnose group of formula α-L-Rhap-1- and (c) a mixture of trirhamnose and monorhamnose groups as defined in (a) and (b) above wherein Rhap is rhamnose.

According to another aspect, the present invention provides an immunoadsorbent composition comprising an insoluble carrier and an antibody capture agent immobilized to the surface of said insoluble carrier. The antibody capture agent comprises a rhamnose moiety selected from (a) a trirhamnose group of formula α-L-Rhap(1→2) α-L-Rhap(1→2)α-L-Rhap-1- and (b) a monorhamnose group of formula α-L-Rhap-1-, wherein Rhap is rhamnose.

According to a further aspect, the present invention provides an immunoadsorbent composition comprising an insoluble carrier and a trirhamnose monoclonal antibody against group B streptococcus antigen coated on a surface of said carrier at a coating density of no greater than about 160 ng/unit area of said surface.

According to yet another aspect, the present invention provides an antibody isolated from a sheep polyclonal antibody against GBS polysaccharide antigen.

BRIEF DESCRIPTION OF THE DRAWINGS

The invention will now be described with reference to the accompanying drawings, in which.

DETAILED DESCRIPTION OF THE INVENTION

Figure 1:
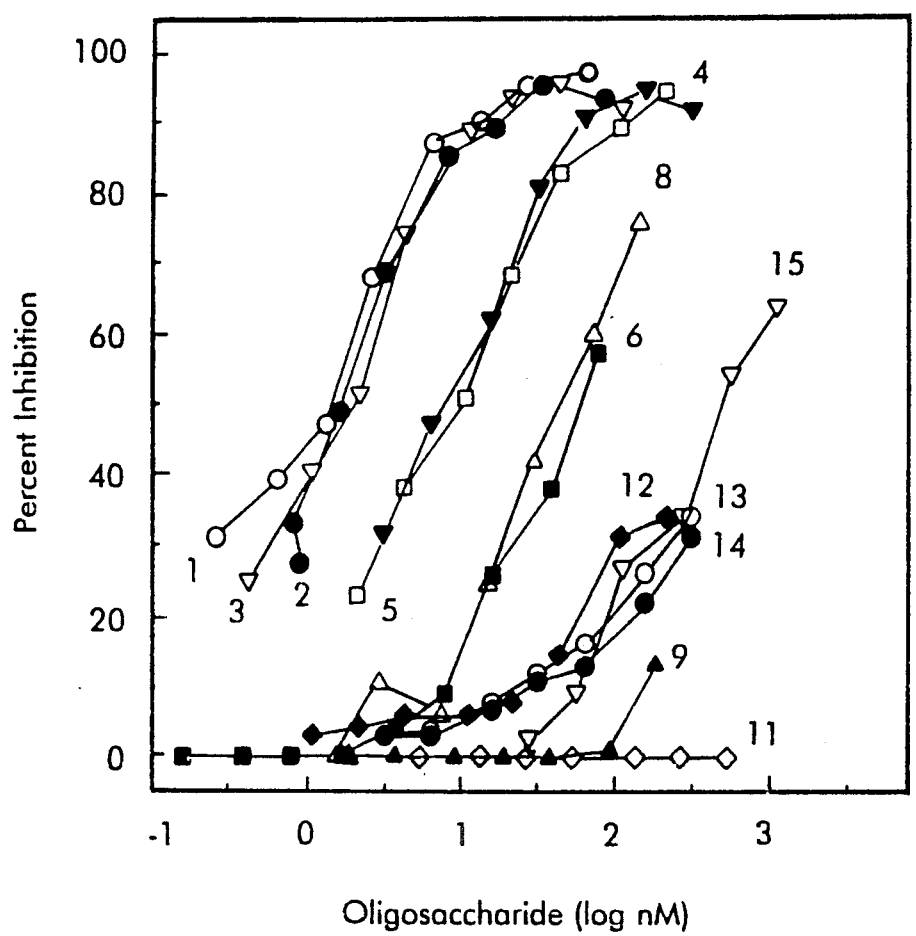
FIG. 1 shows quantitative precipitation inhibition of binding of the group B polysaccharide to polyclonal anti-rabbit group B polysaccharide-specific serum (090R) using various oligosaccharides having the structures 1-22 shown in Table 4.

The following expressions, in the context of the present invention, are to be understood as follows:

i) "immunoadsorbent composition" is a reference to a material which is able to take up a substance involved in an immunoreaction (for example, an antibody or an antigen, as the case may be);

ii) "immunoassay agent" is a reference to any material which is able to participate in the testing of the presence of a substance involved in an immunoreaction (for example, an antibody or an antigen, as the case may be);

iii) "immunogen conjugate" is a reference to a material which when introduced into an animal (for example, a mammal or bird) stimulates or induces the production or development of antibodies thereto;

iv) "antigen capture agent" refers to any substance which can bind to an antigen (for example, an antibody);

v) "antibody capture agent" refers to any substance which can bind to an antibody (for example, an antigen);

vi) "affinity for binding" generally characterizes an element as being able to interact with another element such that the two are bound together;

vii) "affinity for specifically binding" generally characterizes an element as being able to interact with another element in an exclusive or at least dominant fashion, i.e. sufficient for the purposes herein;

viii) "antigen capture agent has an affinity for specifically binding to trirhamnose epitope of group B streptococcus polysaccharide antigen" characterizes the antigen capture agent as being able to interact with the trirhamnose epitope in an exclusive or at least dominant fashion such that any interaction between this capture agent and other components of group B streptococcus polysaccharide antigen (e.g. monorhamnose epitope) is at the very least low or negligible (i.e. the interaction with the trirhamnose epitope is specific enough for the purposes of detection and/or diagnosis of group B streptococcus polysaccharide antigen or group B streptococcus infection);

ix) "antigen marker agent has an affinity for specifically binding to monorhamnose epitope of group B streptococcus polysaccharide antigen" characterizes the antigen marker agent as being able to interact with the monorhamnose epitope in an exclusive or at least dominant fashion such that any interaction between this marker agent and other components of group B streptococcus polysaccharide antigen (e.g. trirhamnose epitope) is at the very least low or negligible (i.e. the interaction with the monorhamnose epitope is specific enough for the purposes of detection and/or diagnosis of group B streptococcus polysaccharide antigen or group B streptococcus infection);

x) "single-site ELISA" refers to an ELISA format assay wherein the epitopic sites targeted by the capture antibody and by the marker (probe) antibody are structurally the same (for example where the trirhamnosyl epitope is targeted by the capture antibody and by the marker antibody); and xi) "two-site ELISA" refers to an ELISA format assay wherein the epitopic sites targeted by the capture antibody and by the marker antibody are structurally different (for example where the trirhamnosyl epitope is targeted by the capture antibody and the monorhamnosyl epitope is targeted by the marker antibody).

The test solution containing the substance (antigen) to be determined may be derived from any source whatsoever. Thus, the source may be a human being or some other animal, such as a mammal or bird. It may, for example, be desired to examine fluids (concentrated as may be necessary by known methods) such as milk, urine, or amniotic fluid. Alternatively, it may be desired to examine gastric swabs, urogenital swabs, placental swabs, bacterial cultures or colonies. The test solution may in particular be derived from vaginal and/or cervical secretions obtained from a swab.

Some GBS polysaccharide antigen may be released naturally by group B streptococcus into a surrounding fluid environment, but this may not result in the presence of a sufficient amount of antigen for detection purposes. An extraction procedure may therefore be required for dislodging GBS polysaccharide antigen from the intact bacteria into the sample fluid.

The extraction procedure generally involves treating the GBS bacteria with a suitable extraction agent which can break the attachment of the GBS polysaccharide antigen to the bacteria cell wall. The extraction conditions such as temperature and extraction agent are selected such that GBS polysaccharide antigen is not adversely affected. The extraction of the GBS polysaccharide antigen may, for example, be carried out in an aqueous medium containing the desired extraction agent, which may consist of a single compound or may comprise two or more compounds which interact to bring about the extraction. Suitable extraction techniques include, for example, enzymatic methods (22) and the nitrous acid method. In the nitrous acid method, nitrous acid is usually produced in situ by combining together at least two reactants which are capable of reacting when admixed (e.g. in an aqueous medium) to produce nitrous acid. One of the reagents may be selected from an organic acid and the other may be selected from an inorganic nitrite. Any combination of organic acid and inorganic nitrite may be used, provided that the combination is suitable for the nitrous acid extraction of the GBS polysaccharide antigen. The organic acid may, for example, be acetic acid, succinic acid or citric acid. The inorganic nitrite may, for example, be an alkali metal nitrite, e.g. sodium or potassium nitrite.

An example of a known micronitrous acid extraction method for extracting GBS polysaccharide antigen from intact bacteria at ambient temperature and pressure is described by Slifkin, M., et al (23). Using the microtiter well format, it has been found that for this type of extraction about 20 minutes is required to reach a maximal extraction. In practice, 5-10 minutes may be sufficient for detection purposes.

The extraction procedure generally comprises the following steps:

1) incubating a bacteria sample suspected of containing GBS bacteria with a suitable extractant capable of extracting GBS polysaccharide antigen, so as to form an analyte solution;
2) if necessary, after a suitable incubation period has passed, admixing a neutralization agent with the analyte to neutralize any excess extractant;
3) contacting the obtained analyte solution with an antigen immunoadsorbent composition as defined herein;
4) incubating the analyte solution with the antigen immunoadsorbent composition;
5) incubating the GBS polysaccharide antigen taken up by the antigen immunoadsorbent composition with an antigen marker agent having the desired label;
6) washing the thus obtained capture "sandwich" with a suitable washing agent, i.e. an aqueous solution which does not adversely affect the structure of the "sandwich" nor the activity of the bound marker agent;
7) determining the presence of and, if desired, the quantity of, GBS polysaccharide antigen/bacteria, based on the nature of the marker agent taken up by the bound polysaccharide antigen in step 5 above.

The antigen capture agent may, for example, comprise an antibody (monoclonal or polyclonal) or some other equivalent substance such as, for example, lectin. Similarly, the antigen marker agent may, for example, comprise an antibody (e.g. monoclonal or polyclonal) or other equivalent substance which has the necessary affinity for binding to the GBS polysaccharide antigen. Alternatively, the antigen capture agent and the antigen marker agent may comprise a suitable fragment of an antibody such as, for example, a Fab fragment, with the fragment possessing the desired or necessary affinity. These agents may also comprise any suitable single domain antibody (dABs) (13).

The antigen capture agent is immobilized to the carrier by adsorption or covalent bonding so as to insolubilize the antigen capture agent with respect to the test media to which the antigen capture agent is to be exposed. The carrier may be of organic or inorganic composition. For example, it may be selected from among amylases, dextrans, natural or modified cellulose, polyethylene, polystyrene, polyacrylamides, agaroses, and silicates such as glass. The antigen capture agent may, for example, be immobilized to the inner wall of test vessels (i.e. to test tubes, microtiter plates, or cuvettes of glass or other materials such as referred to above), as well as to solid bodies (i.e. rods of glass and other materials of various forms and shapes). Preferably, the receptacle used has a high area/volume ratio. The capture antibody may be directly immobilized to the carrier or it may immobilized via the residue of some intermediate substance e.g. glutaraldehyde, protein A or protein G.

Any of the known techniques for immobilizing active substances such as antibodies, antigens, enzymes, ligands etc. to carriers (i.e. for insolubilization thereof) may be used (14). The capture antibody may, for example, be immobilized onto the surface of a carrier comprising a polystyrene microtiter plate, well or tube by contacting the functional surface of the carrier with a buffer solution comprising the antibody (e.g. 0.2 to 0.25 ml of a buffer of pH 9.6, the buffer comprising 0.1M $NaHCO_3$ and 5 to 12 ug/ml of capture antibody) at a suitable temperature and for a suitable period of time (e.g. for 16 hours at 4° C.). After immobilization of the capture antibody, the active surface of the carrier may be subjected to a washing treatment with a suitable washing agent to remove unbound antibody. A neutral wash buffer in which the antibody is soluble may be used for the wash treatment, for example, a 0.02M Tris chloride buffer of pH 7.4, containing 0.15M sodium cloride (hereinafter referred to as TBS), TBS containing 0.05% Tween-20 (hereinafter referred to as TBST), or 0.05M sodium phosphate buffered saline pH 7.4 containing 0.05% Tween-20. Tween-20 is a tradmark for polyoxyethylene sorbitan monolaurate which is available commercially from Atlas Chemical. The so obtained immunoadsorbent composition may then be dried for example at a temperature ranging from room temperature to 37° C. for a time period sufficient for this purpose, typically 1 hr at 37° C., and thereafter store at about 4° C. for subsequent use.

The antigen marker agent must have the necessary affinity for binding to the GBS polysaccharide antigen when bound to the insoluble carrier. The marker agent may have an affinity for binding to any number of different coupling sites which may be available on the bound GBS polysaccharide antigen. The availability of a coupling site depends on the nature of the antigen marker agent and the desired coupling site.

As mentioned earlier, the GBS polysaccharide antigen has 38 monorhamnose epitopes and 4 trirhamnose epitopes. It is therefore preferred for the antigen marker agent to have an affinity for specifically binding to the monorhamnose epitope. In this way, amplification is achieved by bonding a large number of molecules of the label-bearing substance to a single molecule of the substance to be assayed.

Preferably, the antigen marker agent comprises a polyclonal antibody derived from sheep antiserum (e.g., GBS polysaccharide sheep antiserum designated as BCH-402 by IAF BioChem International, Laval, Quebec, Canada), and having an affinity for binding to monorhamnose epitope of the GBS polysaccharide antigen.

The antigen marker agent has a suitable label or tracer component for effecting detection. Any suitable label or tracer used for immunoassays, such as, for example, an enzyme, a radioisotope or fluorescence label, may be conjugated to a marker antibody. The label used will of course dictate the nature of the detection technique.

The label enzyme may be horseradish peroxidase for example hydrogen-peroxide oxidoreductase (EC 1.11.1.7). Horseradish peroxidase may be conjugated to a substance, such as an antibody, by using known reduction amination methods (14, 15). It has, for example, been found by the present inventors that it is advantageous to execute the Tijssen amination method (14) by replacing $NaBH_4$ with the milder reducing agent $NaCNBH_3$ and by using an initial reaction ratio of peroxidase to antibody of 2:1. It has been found that the milder reducing agent gives rise to an approximately 1.2 fold more sensitive antibody-enzyme conjugate as compared to the conjugate obtained using $NaBH_4$. Moreover, the use of the above reaction ratio gives rise to a final ratio of enzyme per antibody of 2.2 when $NaCNBH_3$ is used as the reducing agent, as opposed to 1.6 when $NaBH_4$ is the reducing agent.

The enzyme-antibody conjugate obtained using such methods may be purified to remove any unreacted peroxidase and antibody which may be present by subjecting the conjugate to a dialysis treatment in conventional manner. Alternatively, any remaining reactant(s) may be removed by affinity gel techniques. For example, the antibody-enzyme conjugate may be passed through a column containing a concanavalin A lectin affinity gel which binds horseradish peroxidase and its conjugates, but does not bind free IgG antibody. Thereafter, the so-bound conjugate may be eluted from the column with a suitable eluant and the obtained eluate passed through a column containing a $\alpha$-L-rhamnose-1-affinity gel which will bind the conjugate but not the peroxidase itself. The conjugate may then be eluted from the column with a rhamnose eluant. The obtained eluate is thereafter subjected to dialysis to remove free rhamnose.

The following description of the combination and test kit of the invention refers to the ELISA format. However, it will be understood that the present invention is applicable to any assay format and is not limited to the ELISA format. Thus, the invention may, for example, be embodied in a latex agglutination format or a radioimmunoassay format.

The combination or test kit may, for example, include a test device comprising a receptacle containing the antigen capture agent immobilized to a surface of the receptacle. The combination or test kit may also include a specimen swab adapted to collect a test specimen from the vagina or cervix, and capable of being inserted into a receptacle such as referred to above.

Moreover, the combination or test kit may, depending on the nature of the label of the antigen marker agent, include a detection substrate for detecting GBS polysaccharide antigen associated with the marker agent. The detection substrate may comprise one or more components, depending on the nature of the label used for the marker agent, for example $H_2O_2$ as a first detection substrate component in combination with and 3,3',5,5'-tetramethylbenzidine as a second detection substrate component. The combination or test kit may additionally include a washing agent for washing the immunoadsorbent composition, after incubation with antigen marker agent, to remove unattached antigen marker agent.

In accordance with the present invention, the components of the detection substrate may be present as separate aqueous solutions in respective containers or as a premixed solution in a single container. If presented separately, they may be premixed before use or added separately to a test receptacle.

The present invention also provides an immunoadsorbent composition which may be used as an affinity gel to separate, recover and purify (from a suitable polyclonal antibody), antibody fractions having affinities which make them useful as antigen capture/marker agents. This immunoadsorbent composition comprises an insoluble carrier and an antibody capture agent immobilized to the surface of the insoluble carrier. The antibody capture agent comprises a rhamnose moiety consisting of either (a) a trirhamnose group of formula α-L-Rhap-(1→2) α-L-Rhap(1→2)α-L-Rhap-1- or (b) a monorhamnose group of formula α-L-Rhap-1- wherein Rhap is rhamnose. The trirhamnose immunoadsorbent composition (i.e. the composition wherein the antibody capture agent comprises the trirhamnose group) may be used to treat a solution to adsorb out (i.e. separate or capture) antibodies interacting with the trirhamnose epitope. Similarly, the monorhamnose immunoadsorbent composition (i.e. the composition wherein the antibody capture agent comprises the monorhamnose group) may be used to treat a solution to adsorb antibodies interacting with the monorhamnose epitope.

A monorhamnose antibody immunoadsorbent composition wherein the rhamnose moiety of the antibody capture agent consists of the monorhamnose group may be obtained by coupling L-rhamnose (e.g. from Aldrich Chemical Company Inc., Wisconsin, USA) to Sepharose CL-4B (the trade name of a gel available from Pharmacia Fine Chemicals, Dorval, Quebec, Canada) using known procedures (20, 21).

Alternatively, a monorhamnose antibody immunoadsorbent composition may be obtained starting from a synthesized (4) derivative 5-methoxycarbonyl pentyl-α-L-rhamnopyranoside in the same manner as for obtaining the monorhamnose immunogen conjugate referred to above except that the monorhamnose is coupled to an insoluble carrier as defined herein.

A trirhamnose antibody immunoadsorbent composition wherein the rhamnose moiety of the antibody capture agent consists of the trirhamnose group may be obtained in a similar fashion.

The present invention also provides a process for the preparation of an antibody having a specific affinity for binding to monorhamnose epitope of the GBS polysaccharide antigen, wherein the monorhamnose epitope has the formula α-L-Rhap-1-, in which Rhap is rhamnose. The process comprises the steps of contacting an immune serum, containing a suitable polyclonal antibody, with a monorhamnose immunoadsorbent composition, recovering (by elution) the antibody fraction bound to the composition as eluate, contacting the so-obtained eluate with a trirhamnose immunoadsorbent composition, and recovering the so-treated eluate containing the desired antibody.

The above process can be modified to prepare an antibody having a specific affinity for binding to the above monorhamnose epitope of the GBS polysaccharide antigen and an antibody having a specific affinity for binding to the trirhamnose epitope of the GBS polysaccharide antigen, as defined above. The modified process comprises contacting an immune serum, containing a suitable polyclonal antibody, with a trirhamnose immunoadsorbent composition, and recovering (by elution) from the material bound to the composition respective antibody fractions each containing the desired antibodies.

The present invention additionally provides an immunogen conjugate for stimulating monoclonal or polyclonal antibody production against GBS polysaccharide antigen by injection into a suitable animal (such as a mammal or bird). The immunogen conjugate comprises a carbohydrate coupled to a pharmaceutically acceptable carrier, for example a polymer or protein, such as human serum albumin, bovin serum albumin or tetanus toxoid. The carbohydrate has immunoreactivity for stimulating antibody production against rhamnose epitope of GBS polysaccharide antigen, wherein the rhamnose epitope is selected from (a) a trirhamnose group of formula α-L-Rhap(1→2)α-L-Rhap(1→2)α-L-Rhap-1-, (b) a monorhamnose group of formula α-L-Rhap-1- and (c) a mixture of trirhamnose and monorhamnose groups as defined in (a) and (b) above, wherein Rhap is rhamnose.

The carbohydrate may, for example, comprise the above rhamnose moieties (a), (b) and/or (c). Moreover, the immunogen conjugates may comprise GBS polysaccharide antigen bound to a pharmaceutically acceptable carrier.

In general, any conventional process may be used for conjugating the carbohydrate to the pharmaceutically acceptable carrier. Thus, an immunogen conjugate may be prepared by binding a substance comprising the carbohydrate, e.g. a rhamnose moiety as herein defined, to a suitable pharmacetically acceptable carrier using a process including any necessary activation of the substance and/or carrier to effect binding. For example, a rhamnose moiety may be bound to a carrier by using, as a starting material, the GBS polysaccharide antigen itself. Alternatively, a suitable oligosaccharide unit, fragment or derivative thereof may be used. The oligosaccharide comprising the rhamnose moiety may be derived from the GBS polysaccharide antigen or may be synthesized in accordance with known procedures (6, 7).

The starting carbohydrate material may, for example take the general form as follows:

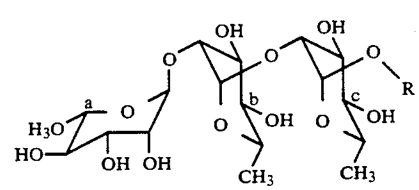

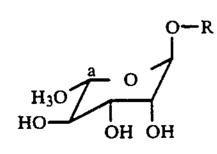

wherein R is H or an organic or reactive moiety. If R is hydrogen, for example it may be desired to bind the rhamnose group to the pharmaceutically acceptable carrier via a suitable spacer group. Activation may be achieved using hydrazine or sodium metaperiodate for subsequent coupling to the carrier (e.g. a protein). R may further be $-(CH_2)_5-COOMe$, D-glucitol or a group of formula:

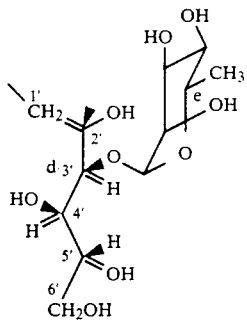

A monorhamnose immunogen conjugate comprising the monorhamnose group may be obtained starting from the synthesized derivative 5-methoxycarbonylpentyl-α-L- rhamnoside (7). This derivative may be activated by hydrazine hydrate and then linked to a suitable protein carrier to obtain a monorhamnose conjugate. A trirhamnose immunogen conjugate, i.e. an immunogen conjugate comprising the trirhamnose group, may be prepared in a similar fashion starting from the corresponding 5-methoxycarbonylpentyl-α-L-trirhamnoside derivative.

Immunogen conjugates, such as described above, may also possibly be used as intermediates for binding of rhamnose groups to insoluble carriers. Antibody immunoadsorbent compositions obtained in this way may be used as serodiagnosis agents, for example in ELISA-type assays. The conjugates may be bound to the surface using any suitable conventional immobilization technique as described above.

The immune serum referred to above may be developed from the blood of any suitable animal (e.g. a mammal or bird) which has been previously exposed, for example, to an immunogen conjugate such as that described above. For example, an immunogen conjugate comprising GBS polysaccharide antigen bound to a pharmaceutically acceptable carrier, e.g. tetanus toxoid, may be used to induce the production of antibody by injecting suitable mice, intraperitoneally, at successive monthly intervals, with an emulsion prepared by mixing a solution of the conjugate in phosphate buffered saline and Freunds complete adjuvant. When the titer of antibodies against GBS polysaccharide antigen are detectable, hybridoma cells may be prepared by the usual methods (16).

In accordance with a preferred aspect of the invention, the antigen capture agent and the antigen marker agent are formated to yield a two-site sandwich-type immunoassay, in which the antibodies have affinities for different respective epitopes of the GBS polysaccharide antigen. Preferably, the antigen capture agent has an affinity for binding to the trirhamnose epitope and the antigen marker agent has an affinity for binding to the monorhamnose epitope. This two-site antibody arrangement allows for increased specificity using the trirhamnose epitope as the capture site and increased sensitivity as a result of using the greater numbers of monorhamnose epitope as the target for the antigen marker agent.

Monoclonal antibodies useful in the present invention may be prepared by using conventional techniques which exploit suitable hybridoma cell lines. Thus, any hybridoma cell line may be employed which produces a monoclonal antibody having the desired affinity for binding to the GBS polysaccharide antigen. The method of Kohler and Milstein (17), for example, may be used for producing monoclonal antibodies. The method of Stahli et al (18) may be used to distinguish monoclonal antibodies which are directed against different epitopes of the same antigen.

If the antigen capture agent is to comprise a monoclonal antibody, the antibody must possess the necessary affinity for binding to the trirhamnose epitope of the group B streptococcus polysaccharide antigen. Subject to the above characteristic, the monoclonal antibody may be of any isotype.

The monoclonal antibody GBS1/18:6/D1 is an example of a monoclonal antibody which recognizes the trirhamnose epitope of the GBS polysaccharide antigen and, preferably, may be used as capture antibody. This antibody is of the IgG3 isotype and has been found to interact with serotypes Ia, Ib, Ic, II and III of GBS (16). This antibody is alternatively designated as BCH-406 by IAF BioChem International Inc., Laval, Quebec, Canada. The cell line designated as BEH-406 which produces the antibody was deposited with the American Type Culture Collection, situated at 12301 Parklawn Drive, Rockville, Maryland, 20852, on April 6, 1993, and has been accorded the accession number ATCC HB11321.

The IgG3 monoclonal antibody referred to above may also be obtained from ascites (mouse or other suitable animal) using known techniques (16). The obtained IgG3 monoclonal antibody may be purified from ascites fluid by protein A affinity chromotography using the method of Ey, P.I., et al (19). Thus, for example, ascitic fluid may be produced by exploiting in known manner the hybridoma cell line designated as BCH-136 (by IAF BioChem International Inc., Laval, Quebec, Canada) which secretes the IgG3 antibody referred to above. Samples of ascites fluid prepared with this hybridoma may be purified by protein A affinity chromatography using a protein-A Sepharose-4B column. In accordance with the present invention, it has been found that eluting from this type of column was possible at a pH of 4.5 with a yield of 2.1 mg IgG per ml of ascites.

Antibodies useful for either for the antigen capture agent or for the antigen marker agent may alternatively be produced by first injecting into the body of a suitable animal an effective amount of a stimulant to illicit the desired production of antibody for the GBS polysaccharide antigen, and subsequently recovering the desired antibody from the animal's antiserum. The animal may, for example, be selected from rabbits, horses, goats, guinea pigs, mice, cows, sheep, or hens. The stimulant may comprise a suitable immunogen conjugate such as described herein. The desired antibody may be purified from the antiserum by using conventional techniques which may involve the use of an antibody immunoadsorbent composition also as described herein.

Binding inhibition studies conducted by the present inventors have shown that the BCH-406 monoclonal antibody is highly specific for the trirhamnose epitope [α-L-rhamnose-(1→2)rhamnose (1→2) rhamnose-1]. Interaction with the dirhamnose [rhamnose(1→2)rhamnose-1-] has been found to be only 1/20th as effective while interaction with free rhamnose has been found to be negligible.

The inventors have also found from studies of the specificity of affinity purified sheep polyclonal antibody that it is able to interact equally with two separate rhamnose containing epitopes, the rhamnose (1-3) galactose and the rhamnose (1-3) glucitol structure, which together number 30 moles/mole of antigen. This represents a 10 fold greater number of potential labeled antibody attachment sites than would be available if the trirhamnosyl epitope were employed alone in a single site ELISA. Indeed a 4.2 greater signal was observed with the two-site ELISA than with the single-site ELISA shown in FIG. 7A and 7B (discussed later) at the 0.37 ng antigen concentration.

The test solution, e.g. sera or analyte, suspected of containing GBS polysaccharide antigen may be contacted and incubated with an antigen immunoadsorbent composition under incubation conditions conducive for binding polysaccharide antigen to the immunoadsorbent composition. Thereafter, detection is effected according to known techniques (14) by bringing a suitable antigen marker agent (e.g. a polyclonal antibody-enzyme complex specifically expressing terminal α-L-rhamnose) into contact with the so-bound polysaccharide antigen and incubating the two together so that marker agent binds in "sandwich" fashion to polysaccharide antigen bound to the immunoadsorbent composition. In this way, the bound polysaccharide antigen is exposed to an amount of antigen marker agent which is sufficient to provide the desired sensitivity. After incubation, any excess marker agent is removed by washing with a suitable wash buffer. The presence of GBS polysaccharide antigen may be determined by exposing enzyme coupled to any bound GBS polysaccharide antigen to a suitable detection substrate. The presence or absence of the antigen is noted by the presence or absence of a color change. The amount of bacteria present may be determined with the aid of a calibrated color chart for comparison with the color developed in the test, or with the aid of a spectrophotometer and a standard curve of antigen.

In accordance with the present invention, an ELISA-type assay may, for example, be carried out, by (a) placing a bacterial sample (e.g. a specimen swab comprising suspect bacteria) into a test receptacle, having a suitable antigen capture agent immobilized to the interior surface of the receptacle; (b) adding an aqueous solution of sodium nitrite and an aqueous solution of acetic acid; (c) incubating the swab with the extraction mixture thus obtained at room temperature for about 5 to 20 minutes, intermittently mixing the mixture; (d) adding a neutralizing agent such as, for example, a solution of 0.2M Tris chloride, pH 7.4 containing 0.2% Tween-20; (e) adding the desired antigen marker agent having the desired enzyme label; (f) incubating the mixture thus obtained in the receptacle at room temperature for a suitable time period (e.g. 10 to 15 minutes), intermittently mixing the mixture; (g) removing the swab, if still present, as well as the resulting solution from the receptacle and washing the interior surface of the receptacle with TBST, discarding any wash solution; (h) adding an enzyme detection substrate to the washing receptacle; (i) incubating the enzyme detection substrate mixture in contact with the interior surface of the receptacle at room temperature for a suitable time period (e.g. 10 to 20 minutes) if desired, with intermittent mixing, (j) visually inspecting the obtained mixture in the receptacle for coloration change indicative of the presence of GBS polysaccharide antigen/bacteria and/or, (k) proceeding with an absorbance check (using a spectophotometer in known manner) to note color changes, the check being preceded, if desired, by admixing with the mixture an inorganic acid in an amount sufficient to suspend the enzyme/substrate activity, (for example, $H_2SO_4$) in an amount sufficient to provide a final acid concentration of 0.5N; 50 to 100 ul of 1N to 3N sulphuric acid). If desired, the swab may be removed before step (d), before step (a) or before (f) above, but preferably after step (f). An extraction step is generally not required where enough antigen is already present in the fluid, for example when cows are being tested since the milk is subjected to a culturing step.

As noted earlier, when the standard strategy of coating maximal amount of capture antibody was followed for the single-site ELISA using the trirhamnosyl epitope, the sensitivity dropped to near zero, in the significant range of $<1$ ng of antigen. While not being bound by any theory, a likely explanation for this is that the limited number (four) of trirhamnosyl epitopes on each GBS polysaccharide antigen become completely bound to the capture antibody and thus unavailable for attachment of the labeled second antibody. It has been found that the ELISA functions, albeit with slight reduction in sensitivity, when the capture antibody density is reduced from 500 ng/well to about 160 ng/well. This apparently spaces antibody binding sites on the well wall such that not all trirhamnose epitope can be bound. It is estimated, from the effect of coating density on the two-site ELISA, where the optimum density is 200 ng/well rather than 160 ng/well (see FIG. 7B), that this reduced coating would cause about a 20% loss of signal. Thus, because of some loss of sensitivity and the need to precisely control capture antibody coating, the trirhamnosyl epitope is less preferred for use in a single site ELISA.

On the other hand, the monorhamnose epitope to which the sheep polyclonal antibody binds is functional in a single site ELISA regardless of antibody coating densities. This is probably because of the much greater number of this epitope per antigen molecule (38 moles/mole). This latter epitope does, however, suffer from the drawback of come cross-reactivity with Pseudomonas aeruginose, albeit only at extremely high concentrations of antigen.

The multisite attachment via the trirhamnosyl epitope is thus a distinct advantage for the two site ELISA. The increase in functional affinity which results from the multivalent binding of antigen to IgG and IgM antibodies has been documented to be of the order of $10^3$ and $10^6$ fold respectively (28). Moreover, multivalent capture of the GBS polysaccharide antigen, potentially by all four trirhamnosyl epitopes, can be expected to significantly increase the functional affinity of the solid phase for the capture of this antigen.

Referring to FIG. 1, there are shown inhibition curves obtained from experiments to inhibit the precipitation of the group B polysaccharide with rabbit polyclonal antiserum using the oligosaccharides shown in Table 4. These were either fragments of the group B polysaccharide (5, 6) or structural homologues of them, and were obtained by synthetic methods (7) or by degradation of the group B polysaccharide (5, 6). Two distinct specificities associated with the polyclonal rabbit GBS antiserum can be identified from these experiments. The first is the dominant specificity associated with terminal 1-2-linked α-L-trirhamnopyranoside and the second is that associated with terminal α-L-rhamnopyranoside. This can be deduced as follows.

Oligosaccharides 1, 2 and 3 are all equally good inhibitors of binding and all contain the 1-2-linked α-L-trirhamnopyranoside epitope. It is to be noted that the aglycone of these trisaccharides is relatively unimportant in their inhibitory properties despite the fact that oligosaccharides 1 and 2 contain additional features of the fragment oligosaccharides that constitute the group B polysaccharide (6).

Removal of a terminal α-L-rhamnopyranosyl residue from oligosaccharides 1 and 3 to give oligosaccharides 5 and 4 respectively considerably reduces their inhibitory properties. Thus, the terminally located 1-2-linkage between the terminal and penultimate α-L-rhamnopyranosyl residues of the trirhamno pyranoside epitope is important to its binding. This was also confirmed by inhibition experiments using oligosaccharides 12, 13 and 14 where the above terminal 1-2-linkage is substituted by a 1-3- or 1-4-linkage. Even changing the terminal α-L-(1-2)-linkage of the entire trirhamnoside epitope as expressed in oligosaccharide 3 for the an α-L-(1-4)-linkage to give oligosaccharide 12 rendered the latter oligosaccharide non-inhibitory for antibodies directed against the α-L-trirhamnopyranoside epitope.

The antibody population based on the terminal α-L-rhamnopyranoside epitope is best identified in the inhibition experiments (see FIG. 1) using oligosaccharides 12, 13, 14 and 15, which all contain this structural feature. Other oligosaccharides used in these experiments also contain this structural feature but their inhibitory properties are more complex because they contain additional epitopic structures. The simple monomeric nature of the α-L-rhamnopyranoside epitope is demonstrated by the fact that methyl α-L-rhamnopyranoside 15 proved to be an equally good inhibitor as oligosaccharides 12, 13 and 14.

FIG. 1 also provides evidence for the presence in the rabbit antiserum of antibodies associated with a third epitope is provided by the inhibitory properties of oligosaccharides 6 and 8. Although like oligosaccharides 12, 13, 14 and 15, oligosaccharide 8 also contains a terminal α-L-rhamnopyranosyl residue, and it is a much better inhibitor than the aforementioned oligosaccharides. Thus, a third epitope specificity can be envisaged which involves both the terminal α-L-rhamnopyranosyl residue of oligosaccharide 8 and additional neighboring glycose components. The fact that terminal α-L-rhamnopyranose is also critical to the third epitope can be ascertained by the fact that its removal from oligosaccharide 8 renders the resultant oligosaccharide 9 completely non-inhibitory. The third epitope is also present in oligosaccharide 6 which is an actual component of the group B polysaccharide.

Figure 2:
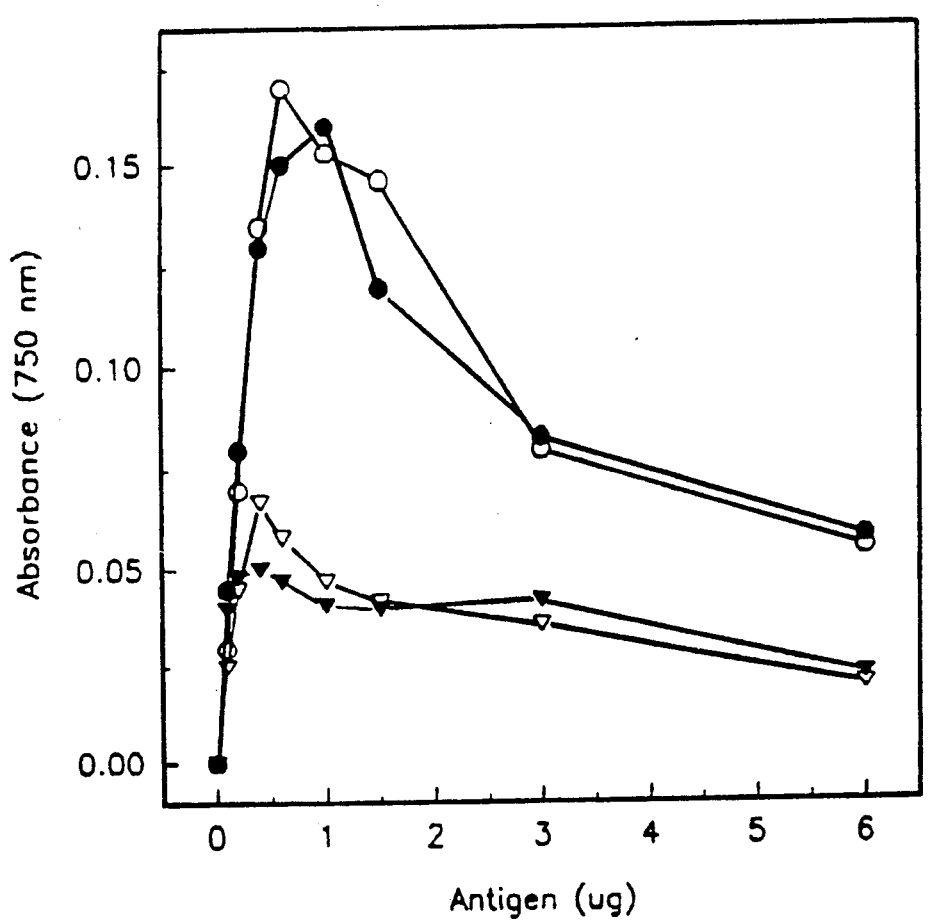
FIG. 2 shows quantitative precipitin curves of the native type Ia (open circles) and type III (closed circles) group B polysaccharides and their respective Naringinase-treated products (open and closed inverted triangles) with the polyclonal anti-rabbit group B polysaccharide-specific serum (090R)

FIG. 2 demonstrates the dominance of the α-L-trirhamnopyranoside epitope in the serology of the polyclonal rabbit antiserum. This was confirmed by quantitative precipitation experiments in which the native group B polysaccharide from two sources, and their Naringinase (α-L-rhamnosidase) treated products (i.e. products obtained by treating group B polysaccharide (10 mg) with 10 units of Naringinase from Penicillium species (EC 3.2.1.40 - Sigma, St Louis, Mo.) were compared. Naringinase is known to specifically remove terminal (1-2)-linked α-L-trirhamnopyranoside from the α-L-trirhamnopyranoside epitopes of the group B polysaccharide (6). The group B polysaccharide obtained from groups Ia and III streptococci gave identical precipitation curves which was also true for their respective Naringinase-treated products. From the precipitin curves, it can be deduced that antibodies specific for the α-L-trirhamnopyranoside epitope constitute approximately two thirds (66%) of the total precipitated antibodies. All other antibodies specific for the group B polysaccharides, including those with a specificity for α-L-rhamnopyranoside, were precipitated by the Naringinase-treated group B polysaccharide.

Figure 3:
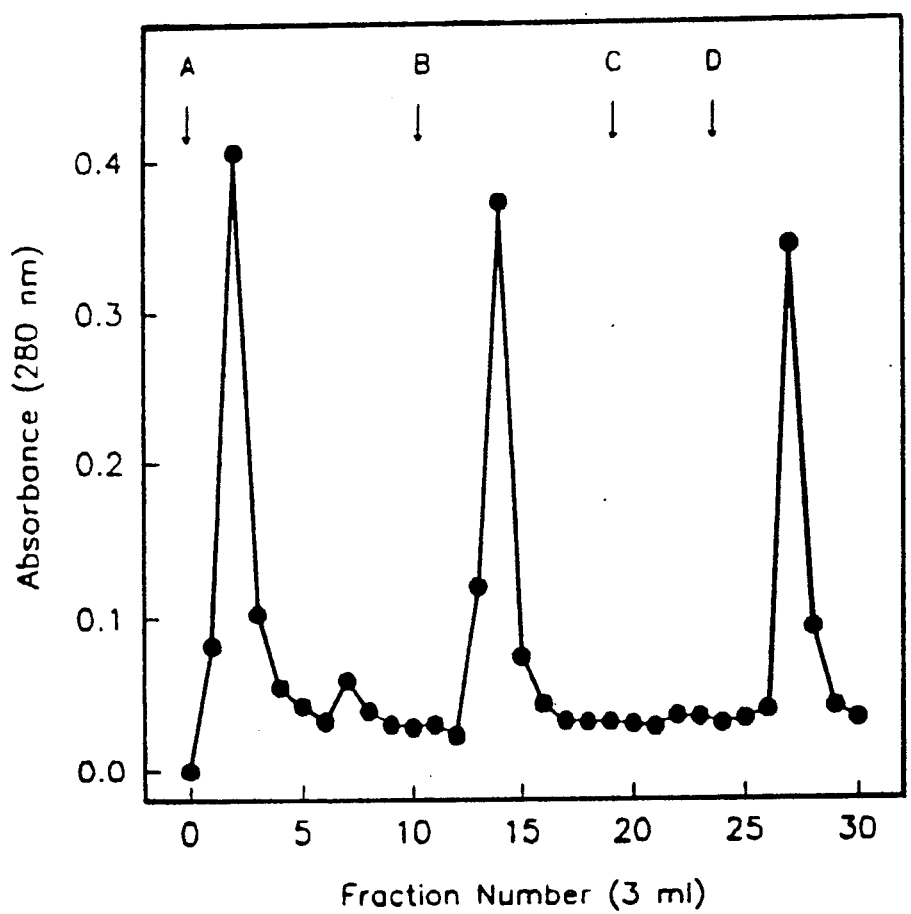
FIG. 3 shows fractionation of the polyclonal anti-rabbit group B polysaccharide-specific serum using an 1-2-linked-α-L-trirhamnopyranoside-affinity column, terminal α-L-rhamnopyranoside-specific antibody being eluted with buffer A and the trirhamnoside specific antibody with buffer D.

FIG. 3 shows the fractionation of the above rabbit antiserum into epitope specificities based on the α-L-trirhamnopyranoside and α-L-rhamno pyranoside epitopes. This was accomplished using an affinity column in which the α-L-trirhamno pyranoside epitope was successfully coupled to a solid support. The α-L-rhamno- pyranoside-specific antibody was eluted from the column using a buffer containing 0.2M α-L- rhamnose. Further elution of the column with glycine-containing buffers of differing alkalinity finally eluted the trirhamno pyranoside-specific antibodies at pH 11.5. The fractions containing the antibodies with the two different specificities were identified by monitoring the fractions by ELISA using an α-L-rhamno pyranoside-conjugate and an α-L-trirhamnopyranoside conjugate as coating antigens.

Figure 4:
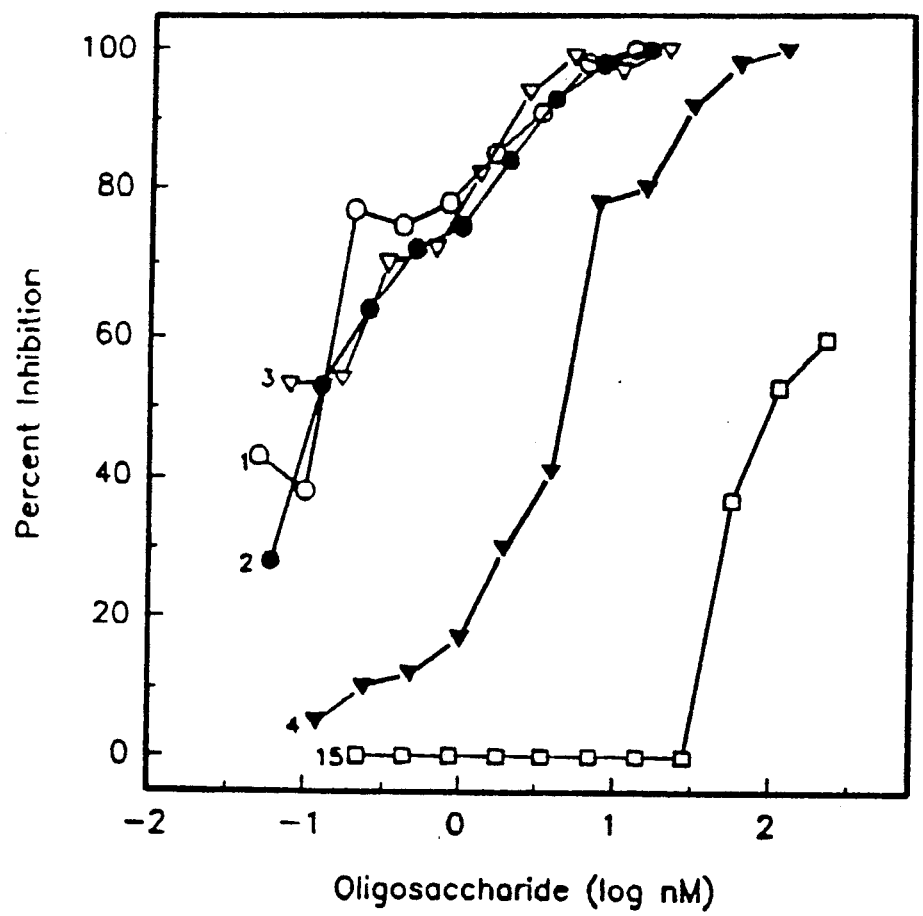
FIG. 4 shows ELISA inhibitions by oligosaccharides 1, 2, 3, 4 and 15 (Table 4) of the binding of trirhamnoside-affinity purified polyclonal anti-rabbit group B polysaccharide-specific serum (090R) with the native group B polysaccharide.

FIG. 4 shows the ELISA inhibition experiments using the affinity-purified α-L-trirhamno pyranoside-specific antibody. Because the group B polysaccharide did not bind to the wells of the ELISA plates, a group B polysaccharide-BSA conjugate was used as the coating antigen. All the oligosaccharides containing the terminal α-L-trirhamnopyranoside epitope (oligosaccharides 1, 2 and 3) were equally good inhibitors of the binding. While the α-L-dirhamnopyranoside (oligosaccharide 4) was a much less potent inhibitor it was nevertheless still able to inhibit the binding. Because the α-L-rhamnopyranoside specific antibody has been previously removed from this antibody fraction as evidenced by the poor inhibitory properties of methyl α-L-rhamno pyranoside, the fact that oligosaccharide 4 still inhibited this fraction of antibodies, indicated that the specificity of this antibody was for the whole α-L-trirhamnopyranoside epitope.

Figure 5:
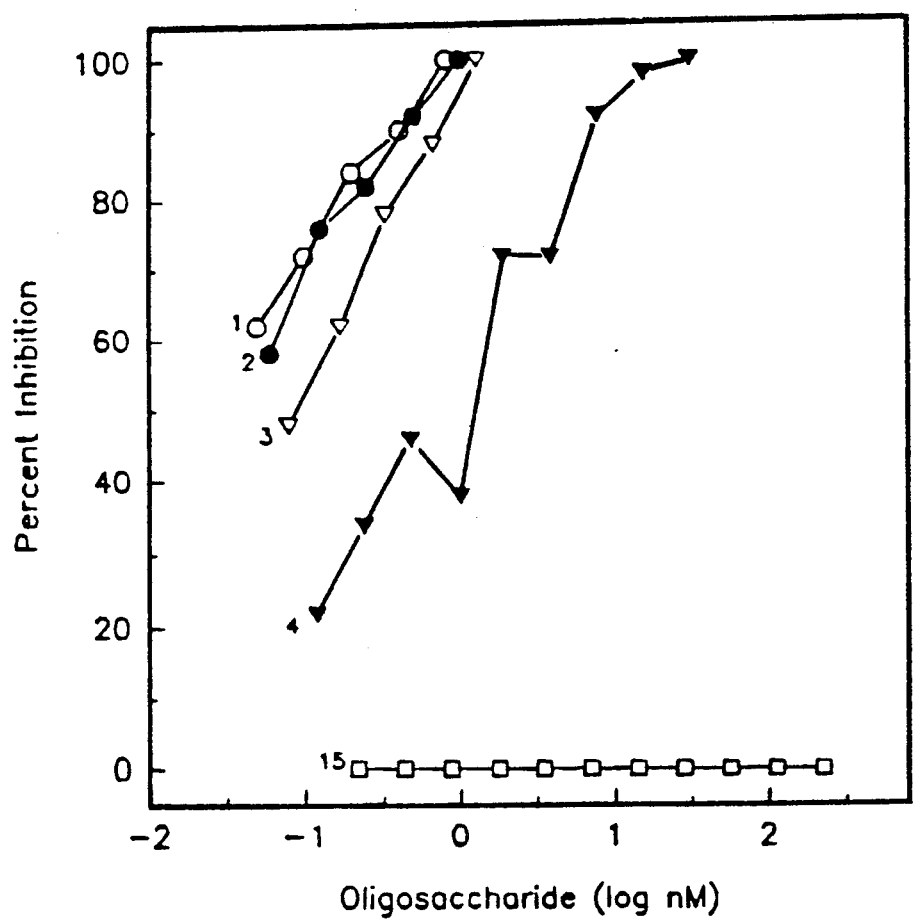
FIG. 5 shows ELISA inhibitions by polysaccharides 1, 2, 3, 4 and 15 (Table 4) of the binding of a murine monoclonal group B polysaccharide-specific antibody (090R) to the native group B polysaccharide.

FIG. 5 shows binding curves obtained from ELISA inhibition experiments using a group B polysaccharide specific monoclonal antibody (16) and the group B polysaccharide-BSA conjugate as coating antigen. Essentially the same results were obtained as for the affinity-purified polyclonal rabbit antiserum above. Again, all the oligosaccharides (1, 2 and 3) containing the terminal α-L-trirhamno pyranoside epitope were good inhibitors and the α-L-dirhamnopyranoside (oligosaccharide 4), while not as potent an inhibitor was still able to function as an inhibitor. Methyl α-L-rhamno pyranoside (31) was a very poor inhibitor of this system.

Antibodies with specificities other than those associated with the trirhamnoside and monorhamnoside epitopes were also identified in the polyclonal rabbit antisera. Oligosaccharides containing the tetrasaccharide α-L-Rhap-(1-3)α-D-Galp(1-3) β-D-GlcpNac(1-4)α-L-Rhapwere, much better inhibitors of the binding of the group B polysaccharide to the above antibodies than could be expected from their terminal monorhamnoside epitopes alone. The tetrasaccharide is a structural feature of oligosaccharides I and II and, therefore, despite the internal location of I and II in the group B polysaccharide, the tetrasaccharide must still be accessible to the immune mechanism.

Figure 6:
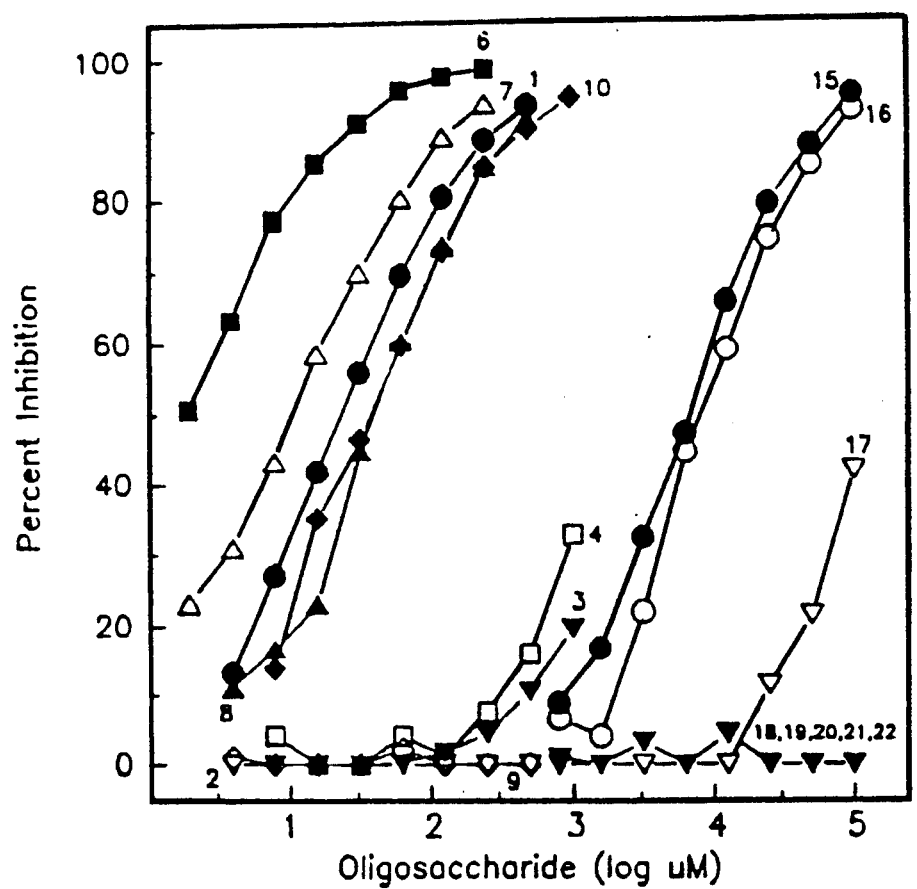
FIG. 6 shows inhibition of the binding of an affinity purified sheep antibody to group B specific polysaccharide.

FIG. 6 relates to the specificity of purified sheep polyclonal antibody. This was evaluated using inhibition ELISA studies employing fragments of the group specific polysaccharides set out in Table 4. To test the inhibitors of antibody binding, the antibody (100 ul) and inhibitor (100 ul) in PBST, were premixed in the wells of a low binding type of microtiter plate (Linbro/Titertek EIA, Flow Laboratories, McLean, USA) for 1 hour at room temperature. A 100 ul volume of this inhibitor-/antibody solution was transferred to the GBS polysaccharide-BSA conjugate coated microtiter wells and incubated for 1 hr. Peroxidase labeled rabbit anti-sheep and enzyme substrate were added as described above. The fragments containing either rhamnose-(1-3)- glucitol (oligosaccharides 1, 7 and 10) or rhamnose-(1-3)-galactose (oligosaccharide 8) were equally effective as inhibitors of the PAb binding to the solid phase group specific polysaccharide-BSA conjugate. Oligosaccharide 6 which contains both rhamnose-(1-3)-glucitol and rhamnose-(1-3)-galactose was considerably more potent as an inhibitor than the fragments containing only one of these sequences. Free rhamnose and the methyl glycoside of rhamnose were both found to be very poor inhibitors requiring a concentration of $1 \times 10^{-1}$M to inhibit similarly to oligosaccharides 1, 6, 7, 8 and 10 at concentrations of $10^{-5}$ to $10^{-4}$M. The inhibition by the monosaccharide, while of a weak nature, seems to be specific since other monosaccharides (glucose, N-acetyl-D-glucosamine) and disaccharides (lactose, melibiose and sucrose) failed to inhibit at concentrations of $1 \times 10^{-1}$M. The oligosaccharides (3 and 4) were both very weak inhibitors indicating that the trirhamnosyl and dirhamnosyl inhibit only as effectively as the rhamnose monosaccharide. Interestingly, galactose was also found to inhibit as well, although it was the least potent of the structures tested. It may be that as the second sugar of the Rha(1-3)Gal(1-3) GlcNAc branch, galactose plays a significant part in the binding of the polyclonal antibody to the group B polysaccharide antigen. Glucitol when tested over a similar concentration range failed to act as an inhibitor, even though the disaccharide containing glucitol, rhamnose-(1-3)-glucitol, was very effective.

Figure 7A:
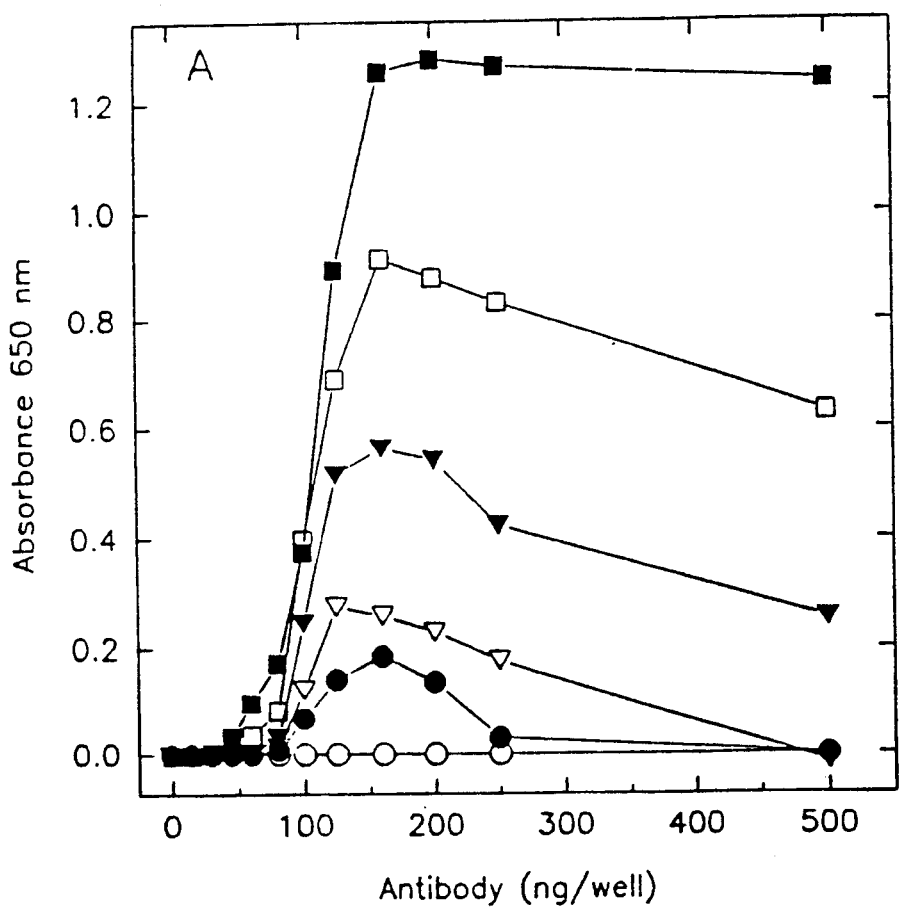
FIGS. 7A and 7B show single-site and two-site ELISA's for detection of group B specific polysaccharide antigen with the trirhamnose specific monoclonal antibody as capture antibody.
Figure 7B:
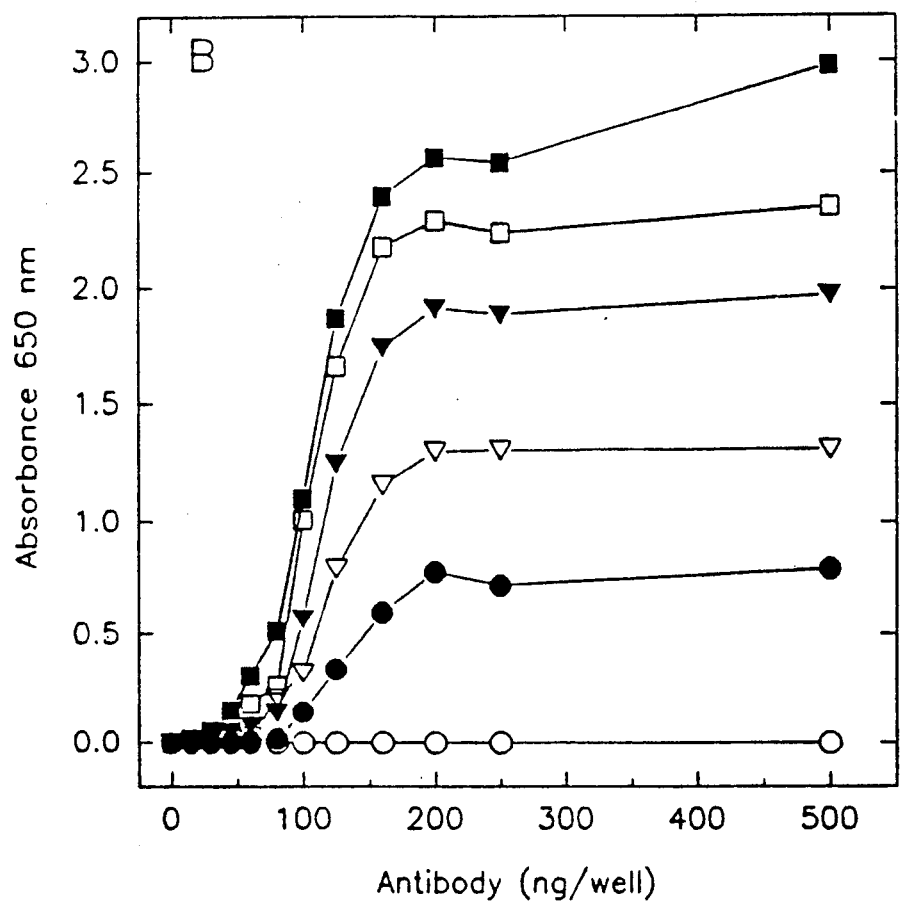

FIGS. 7A and 7B relate to the sensitivity of single-site and two-site ELISAs employing the trirhamnosyl and rhamnosyl containing epitopes. The trirhamnoside specific monoclonal antibody was employed as capture antibody and, in FIG. 7A, the trirhamnoside specific monoclonal antibody labeled with peroxidase was used as the second antibody. In FIG. 7B the affinity purified sheep polyclonal antibody labeled with peroxidase was used as the second antibody. The amount of antibody used to coat each microtiter well is indicated on the x axis, while the amount of group B specific antigen added per well was: 0 ng (open circles); 0.37 ng (filled in circles); 1.11 ng (inverted open triangles); 3.33 ng (filled in inverted triangles); 10 ng (open squares); 100 ng (filled in squares).

The sensitivity as a function of the density of monoclonal antibody coated onto the microtiter wells was found to be biphasic at low GBS polysaccharide concentrations (0.37 ng/test). The maximum signal occurred at 160 ng of Mab per well while at higher coating densities the signal diminished to almost zero. As noted earlier, the most probable explanation for this phenomenon is that multipoint capture of antigen molecules has taken place, (i.e. all 4 trirhamnopyranosyl epitopes being bound to the capture antibody layer) leaving no antigen sites available for attachment of the Mab labeled with peroxidase. An observation which corroborates this interpretation of the data shown in FIG. 7A is that inhibition, which occurs at coating densities above 200 ng/well of Mab, is not seen in the presence of high antigen concentration, i.e. compare the 0.37 ng curve to the 100 ng curve. Under conditions of a large excess of antigen trirhamnosyl epitopes from separate molecules of antigen would be predicted to occupy antibody binding sites of the capture layer. This would leave a possible 3 of the 4 trirhamnoside binding sites on each captured antigen for binding of the peroxidase labeled second antibody. It is evident that the single site ELISA employing the trirhamnosyl epitope is feasible provided that the density of capture antibody is closely maintained at around 160 ng/well or less.

FIG. 7B shows the two-site ELISA, with monoclonal antibody as capture and polyclonal as labeled second antibody. It was found that in contrast to the single-site ELISA described in FIG. 7A, there is no indication of sensitivity to capture layer coating density. Instead, at the 0.37 ng antigen level, the usual linear relation between coating density and signal was apparent until a plateau of the signal occurred as the plastic became saturated. This data indicates a lack of interference by the capture antibody in the attachment of the second labeled antibody which is a result of their different specificities.

Figure 8A:
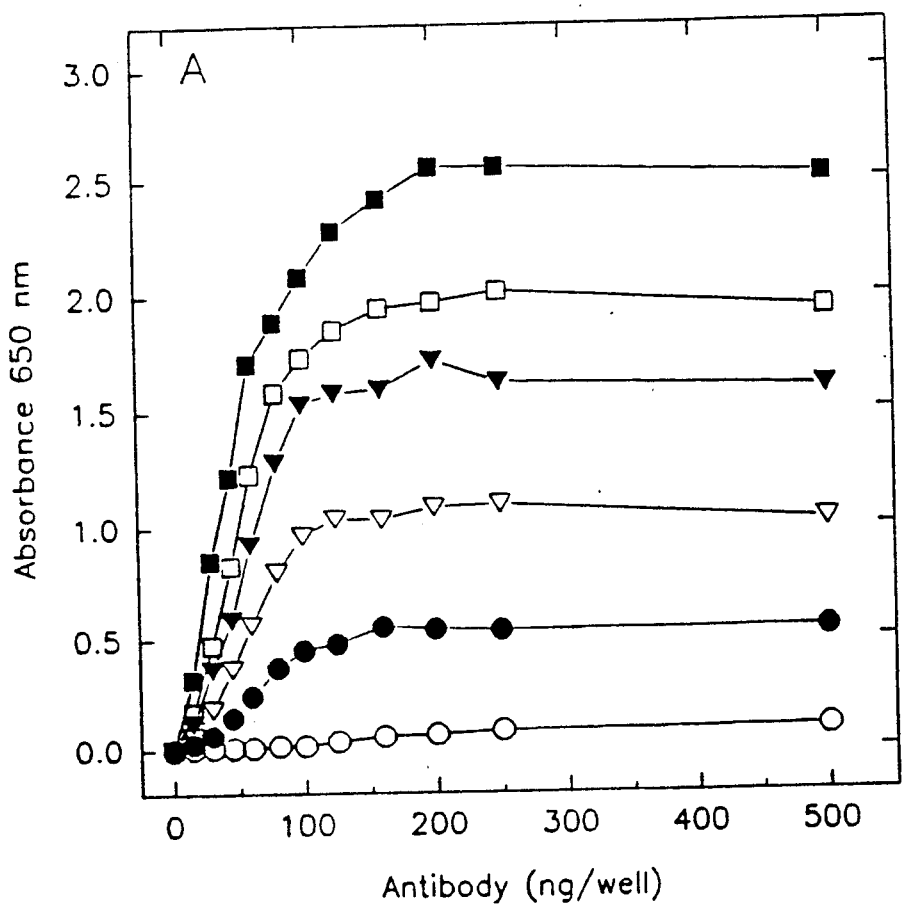
FIGS. 8A and 8B show single-site and two-site ELISA's for detection of group B specific polysaccharide antigen with monorhamnose specific sheep polyclonal antibody as capture antibody.
Figure 8B:
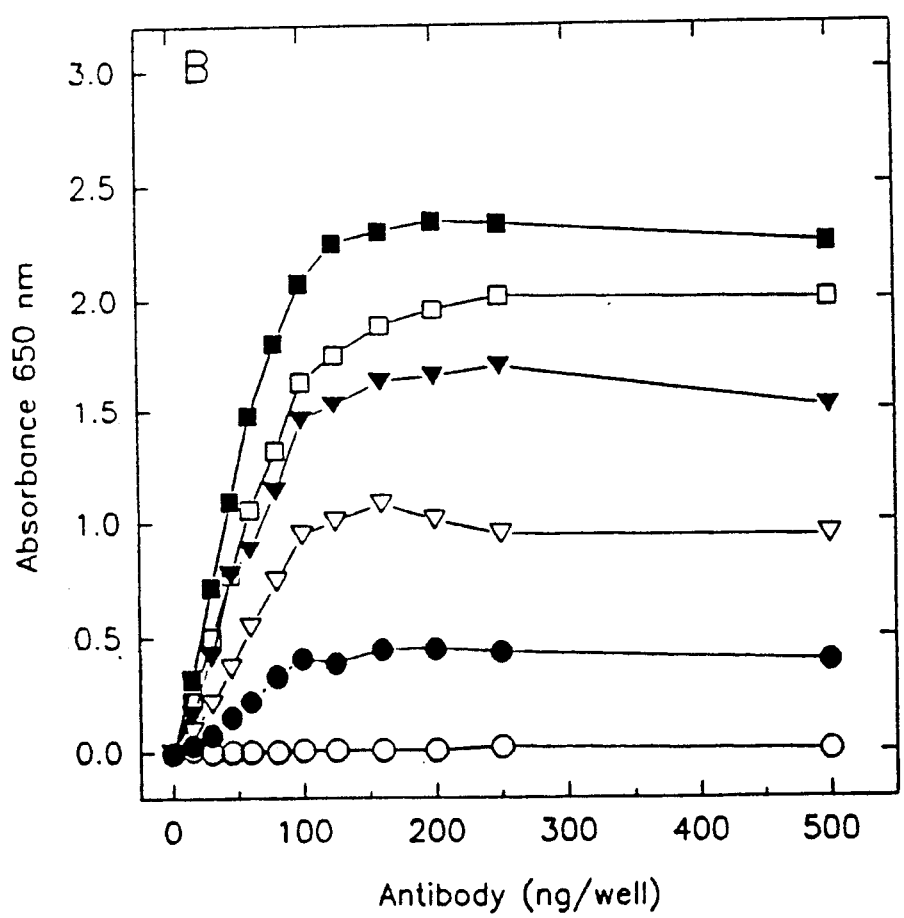

FIGS. 8A and 8B show the result of a similar pair of experiments carried out employing the polyclonal monorhamnose containing epitope for capture of antigen. In neither the single-site ELISA, FIG. 8A, nor the two-site ELISA, FIG. 8B, was there evidence of interference by the capture layer of the attachment of the second peroxidase labeled antibody. Because there are 30 potential binding sites for the polyclonal, 15 Rha(1-3)Gal and 15 Rha(1-3)Glucitol, there appears to be ample sites available for attachment of the peroxidase labeled second antibody, irrespective of the capture antibody coating density.

To detect group B polysaccharide, microtiter plates were coated with 200 ul of a 5 ug/ml solution of the monoclonal or the polyclonal antibody. Antigen in 200 ul of PBST was applied to the wells for 30 minutes which were then washed five times with PBST. Peroxidase labeled second antibody diluted 1/10,000 in PBST was added to each well and after 30 minutes the wells were again washed five times with PBST. Enzyme substrate was added and the absorbance read.

Figure 9:
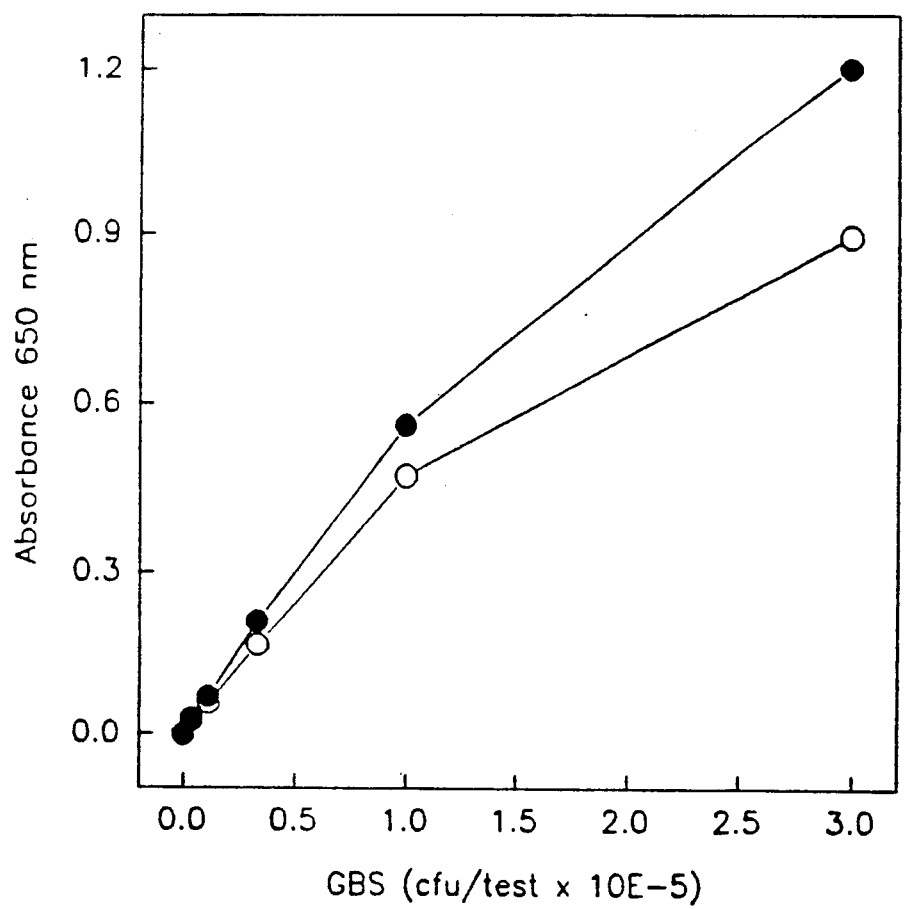
FIG. 9 illustrates the sensitivity of the ELISA for GBS cells, employing as capture antibody the trirhamnose specific monoclonal antibody (open circles) or the monorhamnose specific polyclonal antibody (closed circles) and, in both cases, employing the peroxidase-labelled monorhamnose specific sheep polyclonal as marker antibody.

FIG. 9 shows the relative sensitivities of the two ELISAs shown in FIG. 7B and FIG. 8B, when tested using group B streptococci cells. The serotype III group B streptococcus cells were extracted as described above and transferred to microtiter wells coated was either the trirhamnose specific monoclonal antibody (open circles) or the monorhamnosyl epitope specific polyclonal antibody (closed circles). The two site ELISA, with the trirhamnosyl epitope used for capture, and the monorhamnose containing epitope as attachment site for the peroxidase labelled monorhamnose specific sheep polyclonal as second antibody, was found to have a similar sensitivity to that of the single site ELISA, with the monorhamnose containing epitope as both capture and labeled second antibody. Both ELISA arrangements had the necessary sensitivity to detect the $3 \times 10^4$ cfu which has been correlated with intrapartum infection of infants (1).

Figure 10:
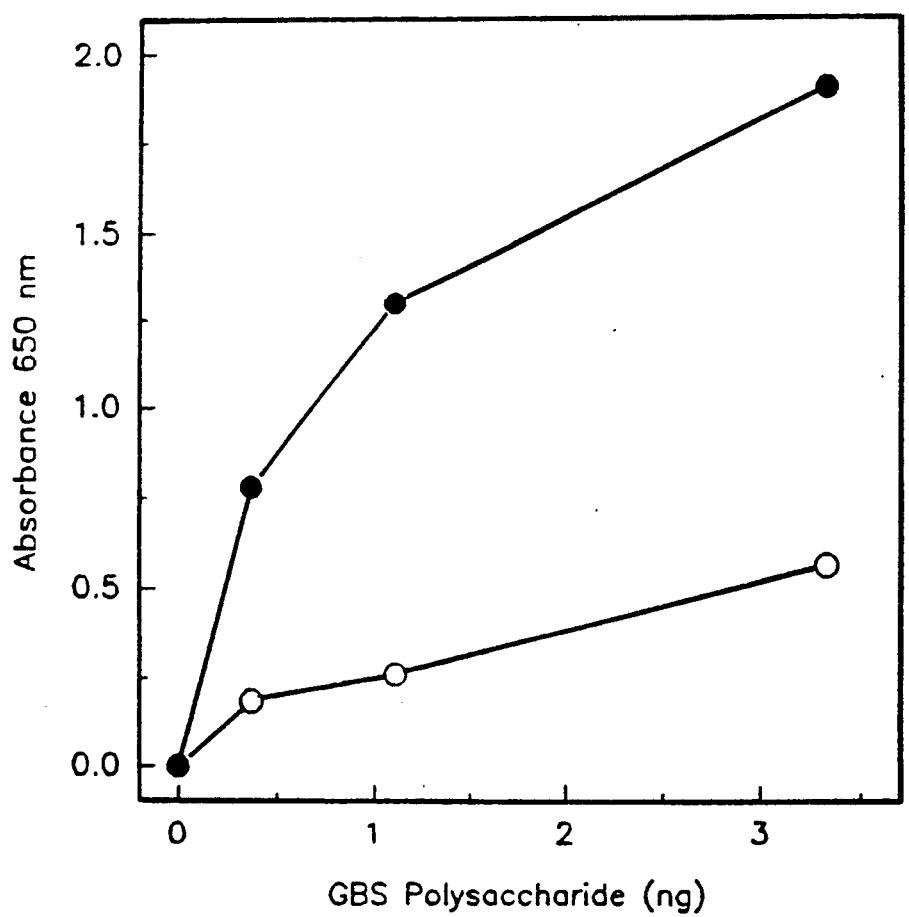
FIG. 10 illustrates the sensitivity of the ELISA employing the trirhamnose specific monoclonal antibody as capture antibody in a single-site ELISA (open circles - data from the 160 ng antibody coating density of FIG. 7A) and in a two-site ELISA using the monorhamnose epitope polyclonal antibody as the labeled antibody (closed circles - data from the 200 ng antibody coating density of FIG. 7B).

FIG. 10 shows the sensitivity of the two ELISAs which use the trirhamnose specific monoclonal for capture antibody. It can be seen that a 4-5 fold gain in sensitivity is obtained when the monorhamnose specific antibody is used as the probe (two-site ELISA closed circles) than when the trirhamnoside specific antibody is used (single-site ELISA open circles).

The sensitivity of the two-site ELISA for actual bacteria is of interest in view of studies which report that $>3 \times 10^4$ cfu of GBS per sample correlates with the occurrence of intrapartum infection of infants (1). As shown in FIG. 9, the two site ELISA is indeed able to detect this number of bacteria and therefore has the sensitivity necessary to be useful in determining which women should receive prophylactic antibiotic treatment.

The specificity of single-site and two-site ELISA's employing the monorhamnose structure as probe epitope and the trirhamnose or monorhamnose as capture epitope was carried out using a library of bacteria representative of the vaginal flora (27). These results are shown in Table 5. Concentrations of $2.4 \times 10^7$ cfu/test, numbers of bacteria above those shown to be recovered on vaginal swabs (27), were tested. The single site ELISA was found to exhibit a major crossreactivity with Pseudomonas aeruginosa (albeit less than 2-fold), a human pathogen not normally a part of the vaginal flora. The organism was barely detected with the two-site ELISA, illustrating its greater specificity. Significant cross-reactivities were not observed with either of the ELISAs.

For the experiments described in the following Examples, representative example cultures of the streptococci bacteria as well as the other bacteria listed in Table 5 below were obtained from the quality control laboratory of the Institut Armand-Frappier (Montreal, Quebec, Canada).

Additionally, conventional methods to culture GBS (in particular, sterotype 18 - WHO No. 123-835) were set up; conventional methods to count bacteria were also set up (24). Solutions containing known numbers of streptococci bacteria and of the other bacteria mentioned in Table 5 were prepared.

EXAMPLES

The invention is now illustrated by the following non-limiting examples.

EXAMPLE 1

Immobilisation of antigen capture agent on polystyrene receptacle carrier to form (antigen) immunoadsorbent composition Polystyrene wells and tubes were treated as follows. The surface of the carrier to be activated was coated with a treatment solution and incubated therewith for 16 hours, at 4° C. The treatment solution was discarded and the treated surface washed 3 times with (1 ml) PBST; 1 time with (1 ml) TBS; and then 2 times with (5 ml) of TBS to remove unbound antibody. The immunoadsorbent composition so obtained was dried (at 37° C. for 1 hour) and then stored with dessicant at 4° C.

For the above immobilisation technique:
(a) as polystyrene carriers (and their corresponding treatment solutions), were used
  Nunc (Nunc inter Med., Denmark) high binding microtiter plates, the treatment solution for the wells thereof comprising 0.2 ml of a sodium bicarbonate buffer (0.1M NaHCO$_3$, pH 9.6), containing 5 ug/ml of antigen capture antibody; and
  Nunc immunotubes, the treatment solution for which comprising 0.25 ml sodium bicarbonate buffer (0.1M NaHCO$_3$, pH 9.6), containing 5 ug/ml of antigen capture antibody; and
(b) as antigen capture antibody (directed against trirhamnose epitope of group B streptococcus polysaccharide antigen) was used IgG3 monoclonal antibody BCH-406 (by IAF BioChem International Inc., Laval, Quebec, Canada) prepared in known manner (16) and purified from ascites fluid on a protein-A Sepharose-4B column (following the method of Ey et al (19).

EXAMPLE 2

Preparation of a trirhamnose (antibody) immunoadsorbent composition: the antibody capture agent comprising the trirhamnose group α-L-Rhap (1->2)α-L-Rhap (1->2)

α-L-Rhap-D-glucitol) was prepared both by synthesis (4) and by aqueous hydrogen fluoride degradation of the group B polysaccharide (3).

α-L-Rhap (1->2)α-L-Rhap (1->2) α-L Rhap-D-glucitol was activated by selectively introducing an aldehyde into the terminal glucitol residue thereof by controlled periodate oxidation (16) by dissolving α-L-Rhap (1->2)α-L-Rhap (1→2) α-L-Rhap- D-glucitol (50 mg) in 1.5 ml of aqueous 0.1M sodium metaperiodate at room temperature. After 10 min. oxidation the reaction was and the solution was left to stand for 20 min at 4° C. The solution was concentrated in a rotary evaporator (<40° C.) and the concentrate was freed of low mw material by its application to a Sephadex 61G column (Pharmacia) eluted with water. The eluate was monitored by a Waters R403 differential refractometer and lyophilization of the fractions of the eluate corresponding to the oxidized oligosaccharide was carried out.

The oxidized trirhamnoside (45 mg) was dissolved in water (3 ml) and reacted with ammonium acetate (500 mg) and sodium cyanoborohydride (50 mg). The reaction mixture was adjusted to pH 9 with 0.1M NaOH and the solution was incubated for 48 h at 37° C. The resultant trirhamonoside containing amino-group was then purified as described for the aldehydic trirhamnoside derivative above. A modified TNBS analysis (30) on the purified amino-functionalized trirhamnoside indicated >90% incorporation of amino-group.

The amino-functionalized trirhamnoside (35 mg) was dissolved in 0.1M sodium bicarbonate buffer (5 ml) and the solution was shaken at 4° C. for 16 h with 5 ml (wet gel) of Affigel 10 (N-hydroxysuccinimide form) (Bio-Rad Laboratories, Richmond, Calif.). The resultant gel was washed with water and PBS and stored at 4° C. resuspended in PBS containing 0.035 sodium azide. The amount of trirhamnoside incorporated (5 mg trirhamnoside/ml wet gel) was estimated from the amount of unreacted oligosaccharide recovered from the aqueous washings of the hapten-linked gel.

EXAMPLE 3

Preparation of a monorhamnose (antibody) immunoadsorbent composition: the antibody capture agent comprising the monorhamnose group L-rhamnose (Aldrich Chemical Company Inc. Wisconsin, USA) was coupled to Sepharose CL-4B (the trade name of a gel available from Pharmacia Fine Chemicals, Dorval, Quebec, Canada) using the procedure of Fornstedt and Porath (20) by incubating 100 ml of Sepharose CL-4B, carefully washed with distilled water, with 100 ml of 0.5M carbonate buffer of pH 11 and 10 ml of a divinyl sulphone bridge (DVS from Aldrich Chemical Company, USA). The mixture was kept at room temperature for 70 minutes under stirring and was subsequently transferred to a glass filter and carefully washed with distilled water. To the activated gel (100 ml) was then added 100 ml of a 20% (w/v) solution of L-rhamnose in 0.5M carbonate buffer of pH 10 and the coupling reaction was allowed to take place overnight at room temperature. The resulting product was extensively washed with distilled water on a glass filter and then suspended in 0.5M bicarbonate buffer of pH 8.5. Two ml of 2-mercaptoethanol was added to each 100 ml of suspension. After 2 hours the product was again recovered and washed carefully with distilled water.

EXAMPLE 4

Preparation of immunogen conjugate(s): Group B streptococcus polysaccharide antigen-protein conjugate(s)

Group B streptococcus (strain ATCC 12400 i.e. strain 090 type Ia, and strain ATCC 12386 i.e. 090R Group B) was grown as previously described (5) and the group B streptococcus polysaccharide antigen was obtained from the culture supernatant by previously described procedures (5). Dilutions of GBS at $10^9$ cfu were prepared by the colony count method.

The group B streptococcus polysaccharide antigen (120 mg) was partially depolymerized with base (5 ml of 0.5M NaOH for 30 min. at 50° C.) and following neutralization of the solution with Rexin 101 ($H^+$) ion exchange resin it was dialyzed and lyophilized. The residue was dissolved in 0.2M ammonium sulfate (2 ml) at pH 8.8 and treated with 10 units of alkaline phosphatase (EC 3.1.3.1) (Millipore Corp., Freehold, N.J.) for 16 h at room temperature. Extraction with cold phenol removed the excess enzyme and the remaining aqueous solution was dialyzed and lyophilized. Introduction of a terminal aldehyde group into the terminal D-glucitol residues of the partially depolymerized group B antigen was accomplished by controlled periodate oxidation (29). The above group B streptococcus polysaccharide antigen (100 mg) was dissolved on water (10 ml) and treated with an equal volume of 0.02M sodium metaperiodate at room temperature for 8 minutes. At this time the excess periodate was destroyed by the addition of ethylene glycol (20 ml) and the solution was allowed to stand for 20 minutes at 4° C. and lyophilized. That the above exposure to periodate did not adversely affect the antigenicity of the group B streptococcus polysaccharide antigen was determined by the ability of the oxidized polysaccharide to still precipitate a group B streptococcus polysaccharide antigen-specific rabbit antiserum in Ouchterlony immunodiffusion experiments.

The oxidized group B streptococcus polysaccharide antigen (50 mg) was dissolved in 1 ml of 0.1M sodium bicarbonate buffer at pH 8.2 and 10 mg of either BSA (Bovine Serum Albumin from Sigma. St. Louis, Mo.) or monomeric TT (obtained from a tetanus toxoid preparation supplied by the Institut Armand Frappier, Laval, Quebec) by a previously described method (29) in 1 ml of the same buffer was added. To this solution was added sodium cyanoborohydride (15 mg) and the solution was magnetically stirred at room temperature for 4 days. The conjugates were purified by gel-filtration using a Bio-Gel A-5m (200-400 mesh) column (1.6×90 cm) (Bio-Rad Laboratories, Richmond, Calif.) using PBS as eluant. Fractions eluting from the column were monitored by a Waters R403 differential refractometer and by U.V. Spectroscopy at 280 nm. Using this column the excess polysaccharide antigen was separated from the conjugates and also a comparison of the elution profile of the conjugation products with that of TT or BSA indicated that all the TT and BSA were conjugated. The fractions containing the group B streptococcus polysaccharide-protein conjugates were individually pooled, dialyzed and lyophilized. The protein content of the conjugates was determined by the method of Lowry (31), and their carbohydrate content by the method of Dubois (32) using the group B streptococcus polysaccharide antigen as standard. The protein/polysaccharide ratio was 1:2.4 for the TT and 1:3.0 for the BSA. The purity of the conjugates was confirmed by FPLC (Pharmacia) using a gel-filtration column (Superose 12 HR10/30, Pharmacia).

A series of bacteria including representative species of the vaginal flora (27) (see Table 5) were prepared by the Institute Armand-Frappier, Laval, Canada. Dilutions of $10^9$cfu/ml in 0.15M NaCl were prepared by the MacFarland optical density method. The bacteria were killed by addition of 2% final concentration of formalin and stored at $-80°$ C. until used. The serotypes of GBS prepared were; streptococcus agalactiae Ia (ATCC 12400), Ib (ATCC 12401), II (ATCC 12973), III (ATCC 12403).

EXAMPLE 5

Preparation of immunogen conjugate(s): a monorhamnose-BSA conjugate and a trirhamnose-BSA conjugate 5-methoxycarbonylpentyl-a-L-rhamno pyranoside and 5-methoxycarbonylbentyl 2-O-[2-O-(α-L-rhamnopyranosyl)-α-L-rhamnopyranosyl]-α-L-rhamnopyranoside were prepared by previously described procedures (7) except that 5-methoxypentyl was substituted for the D-glucitol derivative and used in the production of the equivalent 1-O-D-glucitol-α-L-rhamnopyranoside and 1-O-D-glucitol-α-L- trirhamnopyranoside derivatives.

A solution of the oligosaccharide methyl esters above (100 mg) and hydrazine hydrate (500 ul) in anhydrous ethanol (2.5 ml) was kept at 0° C. for 20 hours. The solution was concentrated under vacuum and finally traces of hydrazine were removed by lyophilization of the products from aqueous solution. The amorphous residues in N,N-dimethylformamide (4 ml) was cooled to $-50°$ C. and nitrogen tetraoxide ($N_2O_4$) (4.6 g) in dichloromethane (100 ml) was added. The temperature was maintained at $-10°$ C. to $-20°$ C. for 15 minutes and then the reaction mixtures were added directly to solutions of BSA (300 mg) in aqueous buffer (20 ml) (pH 9) at 0° C. The solutions were kept at 0° C. for 12 hours then dialyzed and lyophilized. The carbohydrate content of the conjugates was determined by the cystein-sulphuric acid method (27) and indicated the incorporation of approximately 40 haptens per BSA molecule for both conjugates.

EXAMPLE 6

Preparation of antigen marker agent: a polyclonal antibody derivative directed against the monorhamnose epitope, the antibody being conjugated with horseradish peroxidase A) Preparation of Antibody Derivative Polyclonal antisera were raised in a Suffolk sheep immunized intradermally with a 4.5 ml of an emulsion of 2 parts Freunds complete adjuvant (Gibco Laboratories, Grand Island, USA) and 1 part PBS (0.05M Na$_2$HPO$_4$/NaH$_2$PO$_4$, pH 7.4, 0.15M NaCl), containing 0.5 mg of GBS polysaccharide-tetanus toxoid conjugate. This conjugate was found to be more immunogenic than formalin killed group B streptococcus. A large scale bleed was made 74 days after injection: 750 ml of antiserum was separated (in a conventional manner) from the obtained whole blood and the antiserum was stored at −76° C. until required.

An antibody fraction which interacts with the monorhamnose epitope of group B streptococcus polysaccharide antigen was isolated from the above obtained sheep antiserum using the following sequence of steps:

Step 1

Immune serum, 250 ml, was diluted ½ into 2× buffer A and was then passed (5 ml/hr, 4° C.) through a 3.5 cc Rha3 column. The Rha3 column contained 3 cc of a trirhamnose (antibody) immunoadsorbent composition (as described herein) previously equilibrated using a buffer (buffer A) of pH 7.4 comprising 0.05M NaH$_2$PO$_4$Na$_2$HPO$_4$ 0.3M NaCl and 0.01% NaN$_3$;

Step 2

The fluid fractions which passed through the Rha3 column of step 1 were combined and were passed (12 ml/hr 4° C.) through the bed of a Rha1 column. The Rha1 column contained a bed of 15 cc of a monorhamnose (antibody) immunoadsorbent composition (as described herein) previously equilibrated using buffer A. Elution of the bed with 0.1M α-L-rhamnose in buffer A caused a (monorhamnose binding) fraction to emerge between the first and 9th bed volume of elution. This (monorhamnose binding) fraction, 119 ml, containing 556 mg of protein was dialyzed seven times against 2 L of buffer to remove all traces of α-L-rhamnose;

Step 3

The dialized (monorhamnose binding) fraction obtained from step 2 was applied to another Rha3 column as described in step 1 above. The fraction which passed through the Rha3 column was collected and found to contain 401 mg or 81% of the applied protein.

The antibody derivative obtained from the above affinity purification scheme was evaluated (in conventional manner) by gel filtration on a Sephacryl S-300 column. The column (1.6×100 cm) of Sephacryl S-300 superfine (Pharmacia (Canada) Inc., Dorval, Canada) was equilibrated in HBS buffer (0.05M HEPES buffer pH 7.4, containing 0.30M NaCl and 0.01% NaN$_3$). The column was calibrated using a commercial mixture of gel filtration standards with molecular weights ranging from 1,350 to 670,000 daltons (Bio-Rad laboratories, Mississauga, Canada). Purified antibody, 13.8 mg, in HBS was passed through the gel at 5 ml/hr, 4° C., and the position of eluted protein determined by reading the absorbance at 280 nm. A single major peak containing 93% of the applied protein was recovered at the same elution volume as standard IgG. A minor peak emerged at a molecular weight of about 5000 and contained 2% of the applied material. These results indicate that the purification scheme yielded highly pure antibody of the IgG isotype. The specificity of the (polyclonal) antibody derivative was examined and it was found unable to bind bovine serum albumin conjugate of [rhamnose(1-2)rhamnose(1-2)rhamnose] bound to microtiter plates. A strong interaction was, however, observed with conjugates containing [L-rhamnose-1-] or group B streptococcus polysaccharide antigen units. The obtained antibody thus interacts with terminal monorhamnose groups found on the group B streptococcus polysaccharide antigen.

B) Preparation of Antigen Marker Agent

Horseradish peroxidase (i.e. hydrogen-peroxide oxidoreductase, EC 1.11.1.7) was conjugated to the obtained antibody derivative (fraction) using the reductive amination method (15). However, NaCNBH$_3$ was used instead of NaBH$_4$; and a horseradish peroxidase to antibody, initial reaction ratio of 2:1 was also used. Thereafter, a simple dialysis was used to remove any remaining reactants such as NaCNBH$_3$.

EXAMPLE 7

Preparation of antibodies specific for the trirhamnose epitope and specific for monorhamnose epitope Antibodies specific for the trirhamnose epitope and specific for the monorhamnose epitope were obtained (separated and purified) by subjecting a suitable rabbit antiserum to an affinity chromatography treatment using a trirhamnose (antigen) immunoadsorbent composition such as referred to above, as follows:

a) Preparation of Rabbit Antiserum

New Zealand white rabbits were immunized with formaldehyde-killed whole organisms (strain 090R/ATCC 12386) according to the method of McCarty and Lancefield (33). The mouse IgG3 monoclonal antibody directed against GBS polysaccharide (16), designated GBS1/18:6/D1, was produced in ascites fluid and purified by protein A affinity chromatography. The ascitic fluid was produced by injecting hybridoma cells into pristane primed Balb/c mice.

b) Affinity Purification of Polyclonal Antibody Against Trirhamnoside Epitope

A column (1 cm diameter) containing the trirhamnoside-linked gel (3.5 mL) was equilibrated with PBS. Rabbit antisera diluted 1:1 with PBS was applied to the column at a flow rate of 5 mL/h. The column was subsequently eluted with a series of buffers (A, B, C and D) at 15 ml/h using 5 to 10 bed volumes of each buffer. The elution profile is shown in FIG. 3 and the protein was detected by uv spectroscopy at 280 nm. Antibodies specific for terminal L-rhamnose were eluted by buffer A which contained 0.2M L-rhamnose in PBS. Unidentified protein was eluted by buffer B which consisted of 0.1 M glycine at pH 10.5. Further elution of the column with buffer C (0.1M glycine at pH 11.0) also produced a small amount of unidentified protein. Finally antibodies specific for the trirhamnoside epitope were eluted with buffer D (0.1M glycine at pH 11.5). The specificities of the two antibody fractions eluted by buffers A and D were confirmed by ELISA (see below) using rhamnoside- and trirhamnoside-BSA conjugates, the preparation of which is previously described. While the antibody fraction eluted by buffer A reacted with both conjugtes, that eluted by buffer D reacted only with the trirhamnoside-BSA conjugate. None of the other fractions reacted with either conjugate.

c) Affinity purification of a polyclonal antibody directed against a monorhamnose containing epitope The serum of a sheep taken three months after immunization with a GBS polysaccharide-tetanus toxoid conjugate showed high titers of antibody against the group B polysaccharide-BSA, the trirhamnosyl-BSA and the monorhamnosyl-BSA units. Isolation from this serum of a polyclonal antibody directed against a monorhamnosyl containing epitope is summarized in Table 1.

TABLE 1

Purification of polyclonal antibody to GBS polysaccharide

| Column | Fraction | Protein (mg) | R1 Binding (%) | R3 Binding (%) |
|---|---|---|---|---|
| #1 (R1-gel) | Serum (250 ml) | nd | 100.0 | 100.0 |
|  | Flowthrough | nd | 36.4 | 6.4 |
| #2 (R1-gel) | Flowthrough of #1 | nd | 36.4 | 6.4 |
|  | Bound | (556 mg) | nd | nd |
| #3 (Rha-3) | Bound of #2 | (550 mg) | nd | nd |
|  | Flowthrough | (401 mg) | 28.5 | 0.1 | nd: not determined

Antibody binding to a-L-trirhamno pyranoside was first removed by passage of the serum first through an affinity gel containing a-L-(1-2)-trirhamnopyranoside units. This was carried out by equilibrating a 3.5 ml column of the affinity gel in buffer A (0.05N $Na_2HPO_4/NaH_2PO_4$, pH 7.4, 0.30M NaCl and 0.01% $NaN_3$), and passing the immune serum, 250 ml, diluted into an equal volume of 2 × buffer A through the gel at 5 ml/hr at 4° C. This removed over 93% of the anti-trirhamnosyl binding antibodies. At the same time about 63% of the anti-monorhamnose binding activity was retained by the gel, indicating that the terminal rhamnose of the unbranched (terminal) and/or branched trirhamnose unit (internal) of the polysaccharide antigen (6), represents a major proportion of the anti-monorhamnose binding activity present in the serum. The flowthrough fraction, containing the remainder (about 37%) of the anti-monorhamnose binding activity, was passed through an affinity gel containing monorhamnose units and upon elution with 0.1M L-rhamnose a protein fraction was released which contained 556 mg protein. Following extensive dialysis to remove rhamnose, the eluted protein fraction was repassed through the a-L-(1-2)-trirhamnopyranoside affinity column to remove a small amount of residual (5% of original) anti-trirhamnopyranoside binding antibody. The flowthrough fractions of the second trirhamnosyl column were combined, adjusted to 50% glycerol and stored at −20° C. ELISA measurement using trirhamonosyl-BSA and rhamnosyl-BSA coated microtiter plates was used to determine the recovery of antibodies from the affinity columns. The final purified fraction contained 401 mg of PAb which represented 28.5% of the original anti-monorhamnose binding activity. Passage of the purified antibody through a calibrated gel filtration column demonstrated that the eluted protein was comprised almost entirely (97.9%) of IgG.

EXAMPLE 8

ELISA type assay method for the determination of group B streptococcus (polysaccharide antigen/bacterial) from a specimen swab The test method comprised the following sequence of steps:

1. apply 50 ul of bacterial suspension to a rayon swab (Straplex) and then place the sample swab into an antibody coated immunoassay tube or microtiter plate well. The microtiter wells (Immuno 4, Dynatech Laboratories Inc., Chantilly, USA) were coated with antibody in 0.10M $Na_2HCO_3/NaH_2CO_3$ buffer, pH 9.6, overnight at 4° C., blocked for 1 hr, at 37° C. with PBS containing 0.05% v/v Tween-20 (PBST), washed three times with PBST followed by three times with PBS and dried at 37° C. for 1 hour;
2. add 100 ul of 2M sodium nitrite;
3. add 100 ul of 0.1M acetic acid;
4. wait 5 minutes rotating the swab occasionally;
5. add 50 ul of 0.2M tris chloride pH 7.4 containing 0.2% Tween-20;
6. add 100 ul of peroxidase conjugate solution (comprising 0.02M tris chloride, pH 7.4 0.15M sodium chloride (i.e. TBS) and containing 1% normal sheep serum and 1 ug/mL peroxidase labeled polyclonal antibody derivatives (as described above) as marker agent);
7. wait 10 minutes rotating the swab occasionally;
8. discard the swab and wash the immunoassay tube or microtiter well with (6×) TBS containing 0.05% Tween-20;
9. add a substrate comprising tetramethylbenzidene/hydrogen peroxide according to the method of Bos et al (26);
10. ten minutes thereafter visually inspect the tube/well for the development of blue colour; or 15 minutes thereafter read the microtiter wells at 650 nm using a spectrophotometer made by Bio-Tek Instruments Inc, Vermont: for increased sensitivity 100 ul of 1N sulphuric acid is added and the microtiter plates read at 450 nm. In the case of immunoassay tubes 50 ul of 3N sulphuric acid is added and a transfer of the substrate solution may be made, after addition of the acid, to an uncoated microtiter plate for reading.

To determine antibody binding to antigen 100 ul aliquots of a 2 ug/ml solution of polysaccharide-BSA conjugate were coated. Antibody diluted into PBST (100 ul) was pipetted into each well and after 30 minutes the wells were washed five times with PBST. Rabbit anti-sheep IgG (100 ul) Fc specific, (Jackson Immunoresearch Laboratories Inc., West Grove, USA) was added and after 30 minutes the plates were again washed five times with PBST. An $H_2O_2$/tetramethylbenzidine substrate solution for peroxidase (26) was added to each well and the absorbance at 650 nm was read after 15 minutes.

EXAMPLE 9

Effect of nitrous acid extraction on the determination of group B streptococcus polysaccharide antigen The ELISA described in Example 8, was followed using bacterial test specimens comprising 1 ×10^6 CFU group B streptococcus bacteria; steps 1 to 5, however, were carried out in uncoated microtiter wells and the extraction time of step 4 was varied as indicated in Table 2. At the end of the extraction times indicated in Table 2, the extracts were transferred to microtiter wells coated, as indicated above, with IgG3 monoclonal antibody/BCH-406. The results of the tests are outlined in Table 2 below.

TABLE 2

Effect of time on extraction of group B streptococcal antigen by nitrous acid

| Extraction time (min) | absorbance (650 nm) | absorbance (minus zero time) | extraction (% of max) |
|---|---|---|---|
| 0 | 0.101 | 0.000 | 0 |
| 2.5 | 0.241 | 0.140 | 46.8 |
| 5 | 0.321 | 0.220 | 73.6 |
| 10 | 0.347 | 0.246 | 82.3 |
| 20 | 0.393 | 0.292 | 97.6 |
| 40 | 0.400 | 0.299 | 100.0 |

EXAMPLE 10

The ELISA of Example 8 for streptococcal group B was evaluated using commercially available extracts (Difco Co. Laboratories, Detroit, Mich. USA) derived from streptococcus A, B, C, D, E, F and G bacteria, the extracts containing polysaccharide antigens of each of these types of streptococci. Employing the microtiter well format, it was found that the extract from the streptococcus group B gave an absorbance response of >1.00 (650 nm) in each case over the following range of dilutions of the extracts: 1/50, 1/100, 1/200, 1/400, 1/800, 1/1600 and 1/3200. None of the extracts from the other groups gave a positive signal.

EXAMPLE 11

The ELISA of Example 8 was evaluated using a range of known numbers of formalin killed streptococcus group B serotype 10 (GBS 18) and of Eubacterium lentum (E. lentum). For each test, bacteria in 50 ul of 0.15M NaCl, were applied to a microbiological swab (i.e. Starplex Plain S.09 from Starplex Scientific, Mississauga, Ontario, Canada) immediately before each method 1 assay. The assays were carried out in immunoassay tubes (Nunc) activated as above. A Binax kit was also evaluated for comparison purposes. The results are shown in Table 3 below:

TABLE 3

Detection of Streptococcus Group B and *Eubacterium lentum*

| Bacteria CFU × $10^4$ | | ELISA abs (650 nm) | | Binax* abs (450 nm) | |
|---|---|---|---|---|---|
| | | (total) | (net) | (total) | (net) |
| 0 | (blank) | 0.206 | 0.000 | 0.150 | 0.000 |
| GBS | 1 | 0.634 | 0.428 | 0.184 | 0.034 |
| | 3 | 0.615 | 0.409 | 0.167 | 0.017 |
| | 10 | 2.442 | 2.236 | 0.150 | 0.000 |
| | 30 | >3.000 | >3.000 | 0.560 | 0.410 |
| E. Lentum | 2000 | 0.250 | 0.044 | 0.021 | 0.061 |
| | 4000 | 0.248 | 0.042 | 0.150 | 0.000 |

*"Equate Strep B" kit from Binax, South Portland, Maine. U.S.A. was used, following the assay method outlined in the kit.
net = total absorbance minus blank The amount of Eubacterium lentum expected per (vaginal) swab is about $2 \times 10^7$ CFU: i.e. based on the reported amount of this bacteria indicated as occurring naturally as part of the vaginal flora (34). As can be seen from Table 3 above, using immunoassay tubes, the Eubacterium lentum produced a signal that was barely detectable in this range.

EXAMPLE 12

Inhibition of precipitation experiments were performed using aliquots of 100 μL of a ten-fold dilution in PBS of rabbit antisera mixed with increasing concentrations of inhibitor and allowed to stand for 1 h at 37° C. Group B polysaccharide (0.5 μg), sufficient to precipitate just less than the maximum antibody precipitated in the antigen excess zone, was then added to give a final volume of 200 μL. Quantitative precipitin analyses were then carried out by the method of Kabat and Mayer (35). Aliquots 100 μL of a 10-fold dilution in PBS of rabbit-anti group B polysaccharide-specific serum were mixed with increasing concentrations of polysaccharide in a total volume of 200 μL (adjusted with PBS). The tubes were incubated for 1 h at 37° C. and then for 4 d at 4° C. following which they were centrifuged, washed twice with cold PBS, recentrifuged, and the quantity of antibody protein in the pellets was determined by the method of Lowry et al. (31).

Quantitative precipitation of the polyclonal anti-rabbit group B polysaccharide serum with the homologous group B polysaccharide demonstrated that it contained 1.2 mg of polysaccharide-specific antibody per milliliter.

It will be apparent to those skilled in the art that for each aspect of the invention, variations can be made in such parameters as antigen capture agent, antigen marker agent, marker label, carbohydrate, (insoluble) carrier (including receptacle type), amount of immobilized antigen extraction conditions, area/volume ratio of receptacle type carriers, etc. without departing therefrom.

TABLE 4

STRUCTURE OF OLIGOSACCHARIDE INHIBITORS

1)[a]  α-L-Rhap 1→2 α-L-Rhap 1→2 α-L-Rhap 1→1' D-Glucitol 3'-1 α-L-Rhap
2)  α-L-Rhap 1→2 α-L-Rhap 1→2 α-L-Rhap 1→1' D-Glucitol
3)  α-L-Rhap 1→2 α-L-Rhap 1→2 α-L-Rhap OMe
4)  α-L-Rhap 1→2 α-L-Rhap OMe
5)  α-L-Rhap 1→2 α-L-Rhap 1→1' D-Glucitol 3'-1 α-L-Rhap
6)[b]  α-L-Rhap 1→2 α-L-Rhap 1→2 α-L-Rhap 1→1' D-Glucitol 3'-1 α-L-Rhap
<br>    4
<br>    ↑
<br>    β-D-GlcpNAc
<br>    3
<br>    ↑
<br>    α-D-Galp
<br>    3
<br>    ↑
<br>    α-L-Rhap 7)  α-L-Rhap 1→2 α-L-Rhap 1→1' D-Glucitol 3'-1 α-L-Rhap
<br>    4
<br>    ↑
<br>    β-D-GlcpNAc
<br>    3
<br>    ↑
<br>    α-D-Galp 8)  α-L-Rhap 1→3 α-D-Galp 1→3 β-D-GlcpNAc 1→4 α-L-Rhap OMe
9)  α-D-Galp 1→3 β-D-GlcpNAc 1→4 α-L-Rhap OMe
10)  D-Glucitol 3'-1 α-L-Rhap
11)  β-D-GlcpNAc 1→4 α-L-Rhap OMe
12)  α-L-Rhap 1→4 α-L-Rhap 1→2 α-L-Rhap OMe
13)  α-L-Rhap 1→3 α-L-Rhap OMe
14)  α-L-Rhap 1→4 α-L-Rhap OMe
15)  α-L-Rhap OMe
16)  L-Rhamnose
17)  D-Galactose
18)  D-Glucitol
19)  D-Glucose
20)  N-Acetyl-D-Glucoseamine
21)  α-D-Galp 1→4 D-Glu
22)  α-D-Galp 1→6 D-Glu

[a]Previously designated oligosaccharide III
[b]Previously designated oligosaccharide II

TABLE 5

Comparison of Single-Site and Two-Site ELISA Specifications

| Bacteria | Source | (Abs 650 nm) Single-Site | Two-Site |
|---|---|---|---|
| Streptococcus B | 12403[1] | >2.000 | ≥1.500 |
| Streptococcus A | 19615[1] | .002 | .001 |
| Streptococcus equi | ETA[3] | .011 | .001 |
| Streptococcus pneumoniae | 6305 | .000 | .000 |
| Klebsiella pneumoniae | 13883 | .017 | .000 |
| Gardnerella baginella | 14018 | .005 | .003 |
| Staphylococcus epidermis | 12228 | .045 | .000 |
| Lactobacillus fermentum | LSPQ[2] | .000 | .001 |
| Candida albicans | 10231 | .000 | .001 |
| Eubacterium lentum | 25559 | .017 | .008 |
| Peptostreptococcus anaerobus | LSPQ | .013 | .000 |
| Neiseria gonorrhoeae | 19424 | .000 | .002 |
| Pseudomonas aerugenosa | 27853 | .850 | .046 |
| Escherichia coli (K-12)(C-600) | LSPQ | .059 | .018 |

[1]ATCC American Type Culture Collection, Rockville
[2]LSPQ Laboratories de Sante Publique du Quebec, Ste. Anne de Bellevue, Canada
[3]ETA Ecole Technique Agricole, St. Hyacinthe, Quebec, Canada Whole GBS bacteria were extracted by performing a nitrous acid extraction beforehand in the wells of a low binding microtiter plate (Lindro/Titertek EIA). Bacteria in 200 ul of 0.15M NaCl, 25 ul of 5.6N sodium nitrite and 25 ul of 1.4N acetic acid were combined for 15 minutes and then neutralized with 25 ul of 1.4N Tris chloride, pH 10. A 200 ul aliquot of this extract was transferred to the antibody coated plate to begin the ELISA to detect group B polysaccharide. An aliquot equivalent to $2.4 \times 10^7$ cfu of each extract (100 ul), was transferred to microtiter wells coated with 1 ug of the monorhamnose epitope specific polyclonal antibody (single-site ELISA) or with 1 ug of the trirhamnoside specific monoclonal antibody (two-site ELISA). The peroxidase labeled second antibody was the monorhamnose epitope specific polyclonal antibody in both cases.

REFERENCES

1. Morales, W. J. and Lim, D. (1987) Reduction of group B streptococcal maternal and neonatal infections in preterm pregnancies with premature rupture of membranes through a rapid idenfication test. Am. J. Obstet. Gynecol. 157, 13–16.
2. Lancefield, R.C. 1933. A serological differentiation of human and other groups of hemolytic streptococci. J. Exp. Med. 57: 571–595.
3. Lancefield, R.C. 1934. Serological differentiation of specific types of bovine hemolytic streptococci (group B). J. Exp. Med. 59: 441–4580.
4. Lancefield, R.C. 1938. Two serological types of group B hemolytic streptococci with related but not identical, type-specific substances. J. Exp. Med. 67: 25–40.
5. Michon, F., E. Katzenellenbogen, D. L. Kasper and H. J. Jennings, 1987 "Structure of the Complex group-specific Polysaccharide of group B Streptococcus" Biochemistry, 26:476–486;
6. Michon, F., Brisson, J.-F., Dell, A., Kasper, D.L. and Jennings, H.J. (1988) Multiantennary group-specific polysaccharide of group B streptococcus. Biochemistry, 27, 5341–5351.
7. Pozsgay, V. and Jennings, H.J., 1988 "Synthesis of Oligosaccharides Corresponding to the Common Polysaccharide Antigen of Group B Streptococci" J.Org. Chem. 53:4042–4052.
8. Curtis, S.N. and Krause, R.M. (1964) Antigenic relationship between group B and G streptococcus. J. Exp. Med. 120, 629–637.
9. Heidelberger, M., Davie, J.M. and Krause, R.M. (1967) Crossreactions of the group-specific polysaccharides of streptococcal groups B and G in antipneumococcal sera with special reference to type XXIII and its determinants.
10. Yawn, B.P., Yawn, R.A. and Henning T. (1990) Evaluation in rural practice of a rapid group B streptococcus screening test. Family Practice 22, 122–124.
11. Hoppe, J.E., Lindenau, C. and Hofler, W. (1989) Rapid detection of group B streptococci in vaginal swabs of parturients by latex particle agglutination. Zbl. Bakt. Hyg. A 270, 379–384.
12. Costa-Cruz, O., Sesso, A.M., Shrikrishna, M. and Frank, E. (1990) Pasteurella multocida meningitis. New Jersey Med. 87, 127–129.
13. Ward, E.S. Gussow, D., Griffiths, A.D., Jones, P.T. and Winter, G. (1989) "Binding activities of a repetoire of single immunoglobulin variable domains secreted from Escherichia Coli" Nature 341, 544–546).
14. Tijssen, P. (1985) "Practice and theory of enzyme immunoassays in Laboratory Techniques in Biology and molecular biology" general editors Burdon, R.H. and Van Knippenberg, P.H., Elsevier, New York.
15. Wilson, M.B. and Nakane, P.K. (1978) In: Immunofluorescence and related techniques (W) Knapp, H. Holunbar and G. Wick, eds.) p. 215 Elsevier/North-Holland Amsterdam.
16. Feldman, R.G., Law, S.M. and Salisbury, J.R. (1986) Detection of group B streptococcal antigen in necropsy specimens using monoclonal antibody and immunoperoxidase staining. J. Clin. Pathol. 39, 223–226.
17. Kohler, G. and Milstein, C. (1975) "Continuous cultures of fused cells secreting antibody of predefined specificity" Nature 256, 495).
18. Stahli et al, J. of Immunological Methods, 32, 297–304), 1980.
19. Ey, P.I, Prower, S.J. and Jenkin, C.R. (1978) "Isolation of pure IgG1, IgG2a and IgG2b immunoglobulin from mouse serum using protein-A sepharose" Immunochemistry 15, 429–436.
20. Fornstedt, N. and Porath, J. (1975) Characterization studies on a new lectin found in seeds of vicia ervilia. FEBS LETT. 57, 187–191.
21. Porath, J., Laas, T. and Janson, J.C. (1975) J. Chromatogr. 103. 49.
22. Lammler, C., Prede, C. and Biodel, H. (1986) J. Clin. Microbiology 24, 903–904 "Effective murolytic solubilization of streptococcal - Group - specific antigen".
23. Slifkin M., Freedel, D., and Gil, G.M. (1982) Direct sergrouping of group streptococci: from urogenital and gastric swabs with nitrous acid extraction and the phadebact streptococcus test Am. J. Clin. Pathol. 78, 850–852).
24. Jawetz, E., Melwick, J.L. and Adelberg, E.A. (1987) "A review of medical microbiology" 17th edition, Lange.
25. Wilson, M.B. and Nakane, PIK. (1978) In: immunofluorescence and related techniques (Knapp, W., Holubar, H. and Wick, G., eds.) p. 125. Elsivier/North-Holland, Amsterdam.
26. Bos, E.S., Van der Doelen, A.A., van Rooy, N. and Schuurs, A.H.W.M. (1981) 3,3',5,5'-Tetramethylbenzidine as an ames test negative chromogen for horseradish peroxidase in enzyme immunoassay. J. Immunoassay 2, 187–204.

27. Bartlett, J.G. and Polk, B.F. (1984) Bacterial flora of the vagina: quantitative study, Rev. Infect. Dis. 6, S67-72.
28. Hornick, C.L. and Karush, F. (1972) Antibody affinity III The role of multivalence. Immunochemistry 9, 325-340.
29. Jennings, H.J. and C. Lugowski. 1981. Immunochemistry of groups A, B and C meningococcal polysaccharide-tetanus toxoid conjugates. J. Immunol. 127:1012-1018.
30. Lee, Y.C. 1978 Synthesis of some cluster glycosides suitable for attachment to protein or solid matrices. Carbohydr. Res. 67: 509-514).
31. Lowry, O.H. N.J., Rosebrough, A.L. Farr and R.J. Randell, 1951. Protein measurement with the Folin phenol reagent, J. Biol. Chem. 193: 265-275.
32. Dubois, M., K.A. Gilles, J.K. Hamilton, P.A. Rebers and F. Smith, 1956. Calorimetric method for the determination of sugars and related substances. Anal. Chem. 28: 350-356.
33. McCarty, M. and Lancefield, R. C (1955) Variation in the group-specific carbohydrate of group A streptococci J. Exp. Med. 102: 11-28.
34. Bartlett J.G. Onderdonk, A.B., Drude, E. Goldstein, C, Anderka, A.S. and McCormack, W.M. (1977) Quantitative Bacteriolo Vaginal Flora. J. Infect. Diseases 136, 271-277.
35. Kabat E.A. 1961 Kabat and Mayer's Experimental Immunochemistry, Second Edition, Chas. C. Thomas, Inc., Springfield, Ill., page 241.

We claim:

1. An immunoassay combination, comprising an insoluble carrier, an antigen capture agent immobilized on said insoluble carrier to bind a group B streptococcus polysaccharide antigen to said carrier, and an antigen marker agent to bind to said group B streptococcus polysaccharide antigen captured by said antigen capture agent, wherein at least one of said antigen capture agent and said antigen marker agent is an antibody finding specifically to a trirhamnose epitope of formula $\alpha$-L-Rhap(1→2)$\alpha$-L-Rhap(1→2)$\alpha$-L-Rhap-1, in which Rhap is rhamnose.

2. An immunoassay combination according to claim 1 wherein said antigen capture agent is an antibody having an affinity for binding specifically to a trirhamnose epitope of formula $\alpha$-L-Rhap(1→2)$\alpha$-L-Rhap(1→2)$\alpha$-L-Rhap-1, wherein Rhap is rhamnose, from group B streptococcus polysaccharide antigen, and said antigen marker agent is an antibody having an affinity for binding specifically to a monorhamnose epitope of formula $\alpha$-L-Rhap-1 from group B streptococcus polysaccharide antigen.

3. An immunoassay combination according to claim 2 wherein said antigen capture agent is a monoclonal antibody.

4. An immunoassay combination according to claim 3 wherein said monoclonal antibody is an IgG3 designated as BGS1/18:6/D1, secreted by cell line ATCC HB11321.

5. An immunoassay combination according to claim 2 wherein said antigen marker agent is a sheep polyclonal antibody.

6. An immunoassay combination according to claim 2 wherein said insoluble carrier comprises a receptacle containing said antigen capture agent immobilized into said receptacle.

7. An immunoassay combination according to claim 5 wherein said antigen marker agent is labeled with an enzyme for ELISA, latex agglutination or radioimmunoassay reagents a detectable marker wherein said marker is an enzyme or a radioisotope.

8. An immunoassay combination according to claim 1 wherein said antigen capture agent is an antibody having an affinity for binding specifically to a monorhamnose epitope of formula $\alpha$-L-Rhap-1, wherein Rhap is rhamnose, from group B streptococcus polysaccharide antigen, and said antigen marker agent is an antibody having an affinity for binding specifically to a trirhamnose epitope of formula $\alpha$-L-Rhap(1→2)$\alpha$-L-Rhap(1→2)$\alpha$-L-Rhap-1 from group B streptococcus polysaccharide antigen, wherein Rhap is rhamnose.

9. An immunoassay combination according to claim 8, wherein said antigen capture agent is a sheep polyclonal antibody.

10. An immunoassay combination according to claim 8 wherein said insoluble carrier comprises a receptacle containing said polyclonal antibody immobilized into said receptacle.

11. An immunoassay combination according to claim 8 wherein said antigen marker agent is a monoclonal antibody.

12. An immunoassay combination according to claim 11, wherein said antibody is designated as GBS1/18:6/D1, secreted by cell line ATCC HB11321.

13. An immunoassay combination according to claim 8 wherein said antigen marker agent is labeled with a detectable marker wherein said marker is an enzyme or a radioisotope.

14. An immunoassay combination according to claim 1 wherein said antigen capture agent is an antibody having an affinity for binding specifically to a trirhamnose epitope of formula $\alpha$-L-Rhap (1→2)$\alpha$-L-Rhap(1→2)$\alpha$-L-Rhap-1, wherein Rhap is rhamnose, from group B streptococcus polysaccharide antigen, and said antigen marker agent is also an antibody having an affinity for binding specifically to said trirhamnose epitope.

15. An immunoassay combination according to claim 14 wherein said antigen capture agent and said antigen marker is a monoclonal antibody.

16. An immunoassay combination according to claim 15 wherein said monoclonal antibody is an IgG3 designated as GBS1/18:6/D1, secreted by cell line ATCC HB11321.

17. An immunoassay combination according to claim 16 wherein said insoluble carrier comprises a receptacle containing said antigen capture agent immobilized into said receptacle.

18. An immunoassay combination according to claim 17 wherein said antibody is coated into said receptacle at a concentration of no greater than 160 ng/unit area of said receptacle.

19. An immunoassay combination according to claim 14 wherein said antigen marker agent is labeled with a detectable marker wherein said marker is an enzyme or a radioisotope.

20. An immunoassay method for the detection of group B streptococcus polysaccharide antigen in a specimen, said method comprising the steps of:
(i) contacting a test solution of said specimen suspected of containing group B streptococcus polysaccharide antigen with an antigen capture agent which is an antibody having an affinity for binding specifically to a trirhamnose epitope of formula $\alpha$-L-Rhap(1→2)$\alpha$-L-Rhap(1→2)$\alpha$-L-Rhap-1, wherein Rhap is rhamnose, immobilized on an insoluble carrier; and
(ii) introducing an antigen marker agent which is an antibody having an affinity for binding specifically to a monorhamnose epitope of formula α-L-Rhap-1, to detect the presence of any group B streptococcus polysaccharide antigen captured by said antigen capture agent.

21. A method according to claim 20, wherein said antigen capture agent is a monoclonal antibody.

22. A method according to claim 21, wherein said monoclonal antibody is an IgG3 designated as GBS1/18:6/D1.

23. A method according to claim 20, wherein said antigen marker agent is a sheep polyclonal antibody.

24. A method according to claim 20, wherein said antigen marker agent is labeled with a detectable marker wherein said marker is an enzyme or a radioisotope.

25. An immunoassay method for the detection of group B streptococcus polysaccharide antigen in a specimen, said method comprising the steps of:
(i) contacting a test solution of said specimen suspected of containing group B streptococcus polysaccharide antigen with an antigen capture agent which is an antibody having an affinity for binding specifically to a monorhamnose epitope of formula α-L-Rhap-1, wherein Rhap is rhamnose, immobilized on an insoluble carrier; and
(ii) introducing an antigen marker agent which is an antibody having an affinity for binding specifically to a trirhamnose epitope of formula α-L-Rhap(1→2)α-L-Rhap(1→2)α-L-Rhap-1, to detect the presence of any group B streptococcus polysaccharide antigen captured by said antigen capture agent.

26. A method according to claim 25, wherein said antigen marker agent is a monoclonal antibody.

27. A method according to claim 26, wherein said monoclonal antibody is an IgG3 designated as GBS1/18:6/D1, secreted by cell line ATCC HB11321.

28. A method according to claim 25, wherein said antigen capture agent is a sheep polyclonal antibody.

29. A method according to claim 25, wherein said antigen marker agent is labeled with a detectable marker wherein said marker is an enzyme or a radioisotope.

30. An immunoassay method for the detection of group B streptococcus polysaccharide antigen in a specimen, said method comprising the steps of:
(i) contacting a test solution of said specimen suspected of containing group B streptococcus polysaccharide antigen with an antigen capture agent which is an antibody having an affinity for binding specifically to a trirhamnose epitope of formula α-L-Rhap (1→2)α-L-Rhap(1→2)α-L-Rhap-1, wherein Rhap is rhamnose, immobilized on an insoluble carrier; and
(ii) introducing an antigen marker agent which is also an antibody having an affinity for binding specifically to said trirhamnose epitope, to detect the presence of any group B streptococcus polysaccharide antigen captured by said antigen capture agent.

31. A method according to claim 30, wherein said antigen capture agent and said antigen marker agent is a monoclonal antibody.

32. A method according to claim 31, wherein said monoclonal antibody is an IgG3 designated as GBS1/18:6/D1, secreted by cell line ATCC HB11321.

33. A method according to claim 32, wherein said insoluble carrier is a receptacle and said antibody is coated into said receptacle at a concentration no greater than 160 ng/unit area of said receptacle.

34. A method according to claim 30, wherein said antigen marker agent is labeled with a detectable marker wherein said marker is an enzyme or a radioisotope.

35. An immunoassay method according to any one of claims 20 to 34, wherein the test solution is obtained by treating said specimen with aqueous nitrous acid to extract group B streptococcus polysaccharide antigen from group B streptococcus bacteria present in said specimen.

36. A test kit for the detection of group B streptococcus polysaccharide antigen, said kit comprising:
(a) an antigen capture agent which is an antibody having an affinity for binding specifically to a trirhamnose epitope of formula α-L-Rhap(1→2)α-L-Rhap(1→2)α-L-Rhap-1, wherein Rhap is rhamnose, immobilized on an insoluble carrier;
(b) a first extraction agent for an aqueous nitrous acid extraction of group B streptococcus polysaccharide antigen from group B streptococcus bacteria, said first extraction comprising an organic acid;
(c) a second extraction agent for an aqueous nitrous acid extraction of group B streptococcus polysaccharide antigen from group B streptococcus bacteria, said second extraction agent comprising an inorganic nitrite, said first extraction agent and second extraction agent being capable of reacting together to produce nitrous acid when admixed in an aqueous medium;
(d) a neutralizing agent for neutralizing excess nitrous acid; and
(e) an antigen marker agent which is an antibody having an affinity for binding specifically to a monorhamnose epitope of formula α-L-Rhap-1.

37. A test kit according to claim 36, wherein said antigen capture agent is a monoclonal antibody.

38. A test kit according to claim 37, wherein said monoclonal antibody is an IgG3 designated as GBS1/18:6/D1, secreted by cell line ATCC HB11321.

39. A test kit according to claim 36, wherein said antigen marker agent is a sheep polyclonal antibody.

40. A test kit according to claim 36, wherein said antigen marker agent is labeled with a detectable marker wherein said marker is an enzyme or a radioisotope.

41. A test kit for the detection of group B streptococcus polysaccharide antigen, said kit comprising:
(a) an antigen capture agent which is an antibody having an affinity for binding specifically to a monorhamnose epitope of formula α-L-Rhap-1, wherein Rhap is rhamnose, immobilized on an insoluble carrier;
(b) a first extraction agent for an aqueous nitrous said extraction of group B streptococcus polysaccharide antigen from group B streptococcus bacteria, said first extraction comprising an organic acid;
(c) a second extraction agent for an aqueous nitrous acid extraction of group B streptococcus polysaccharide antigen from group B streptococcus bacteria, said second extraction agent comprising an inorganic nitrite, said first extraction agent and second extraction agent being capable of reacting together to produce nitrous acid when admixed in an aqueous medium;
(d) a neutralizing agent for neutralizing excess nitrous acid; and (e) an antigen marker agent which is an antibody having an affinity for binding specifically to a trirhamnose epitope of formula α-L-Rhap(1→2)α-L-Rhap(1→2)α-L-Rhap-1.

42. A test kit according to claim 41, wherein said antigen marker agent is a monoclonal antibody.

43. A test kit according to claim 42, wherein said monoclonal antibody is an IgG3 designated as GBS1/18:6/D1, secreted by cell line ATCC HB11321.

44. A test kit according to claim 41, wherein said antigen capture agent is a monoclonal or polyclonal antibody.

45. A test kit according to claim 41, wherein said antigen marker agent is labeled with a detectable marker wherein said marker is an enzyme or a radioisotope.

46. A test kit for the detection of group B streptococcus polysaccharide antigen, said kit comprising:
   (a) an antigen capture agent is an antibody having an affinity for binding specifically to a trirhamnose epitope of formula α-L-Rhap (1→2)α-L-Rhap(1→2)α-L-Rhap-1, wherein Rhap is rhamnose, immobilized on an insoluble carrier;
   (b) a first extraction agent for an aqueous nitrous acid extraction of group B streptococcus polysaccharide antigen from group B streptococcus bacteria, said first extraction comprising an organic acid;
   (c) a second extraction agent for an aqueous nitrous acid extraction of group B streptococcus polysaccharide antigen from group B streptococcus bacteria, said second extraction agent comprising an inorganic nitrite, said first extraction agent and second extraction agent being capable of reacting together to produce nitrous acid when admixed in an aqueous medium;
   (d) a neutralizing agent for neutralizing excess nitrous acid; and
   (e) an antigen marker agent which is also an antibody having an affinity for binding specifically to said trirhamnose epitope.

47. A test kit according to claim 46, wherein said antigen capture agent is a monoclonal antibody.

48. A test kit according to claim 47, wherein said monoclonal antibody is an IgG3 designated as GBS1/18:6/D1, secreted by cell line ATCC HB11321.

49. A test kit according to claim 48, wherein said insoluble carrier is a receptacle and said antibody is coated into said receptacle at a concentration no greater than 160 ng/unit area of said receptacle.

50. A test kit according to claim 46, wherein said antigen marker agent is a monoclonal or polyclonal antibody.

51. A test kit according to claim 46, wherein said antigen marker agent is labeled with: a detectable marker wherein said marker is an enzyme or a radioisotope.

52. A test kit according to claim 36, 41 or 46, wherein said organic acid is selected from the group consisting of: acetic acid, succinic acid and citric acid, and wherein said inorganic acid is selected from the group consisting of sodium nitrite and potassium nitrite.

53. A test kit according to claim 52, wherein said insoluble carrier is a receptacle, said kit further including a specimen swab for collecting a test bacterial specimen from the vagina or cervix of a patient, said swab being capable of being inserted into said receptacle.

54. A test kit according to claim 53, further comprising f) a washing agent for washing said insoluble carrier after incubation with antigen agent to remove unbound antigen marker agent, and g) a detection substrate comprising:
   (i) $H_2O_2$ for use as a first detection substrate component, and
   (ii) 3,3',5,5'-tetramethylbenzidine for use as a second detection substrate component in combination with said first detection agent.

55. An isolated, purified antibody having affinity for binding specifically to a monorhamnose epitope of formula α-L-Rhap-1, but being devoid or substantially devoid of affinity for a trirhamnose epitope of formula α-L-Rhap(1→2)α-L-Rhap(1→2)α-L-Rhap-1.

* * * * *